United States Patent
Clary et al.

(10) Patent No.: US 9,243,004 B2
(45) Date of Patent: Jan. 26, 2016

(54) SYNTHESIS OF BORONIC ESTERS AND BORONIC ACIDS USING GRIGNARD REAGENTS

(75) Inventors: Jacob W. Clary, Santa Cruz, CA (US); Bakthan Singaram, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/234,382

(22) PCT Filed: Jul. 20, 2012

(86) PCT No.: PCT/US2012/047584
§ 371 (c)(1),
(2), (4) Date: Apr. 25, 2014

(87) PCT Pub. No.: WO2013/016185
PCT Pub. Date: Jan. 31, 2013

(65) Prior Publication Data
US 2015/0119580 A1    Apr. 30, 2015

Related U.S. Application Data

(60) Provisional application No. 61/510,991, filed on Jul. 22, 2011.

(51) Int. Cl.
*C07F 5/04* (2006.01)
*C07F 5/02* (2006.01)

(52) U.S. Cl.
CPC .. *C07F 5/04* (2013.01); *C07F 5/025* (2013.01)

(58) Field of Classification Search
CPC ........................................................ C07F 5/04
USPC .................................................... 549/213, 4
See application file for complete search history.

(56) References Cited

U.S. PATENT DOCUMENTS

| 2003/0100792 | A1 | 5/2003 | Koch et al. |
| 2011/0282090 | A1 | 11/2011 | Dunach et al. |

FOREIGN PATENT DOCUMENTS

| EP | 1285924 A1 | 2/2003 |
| JP | 2002-47292 A | 2/2002 |
| SU | 1220317 A1 | 9/1990 |
| WO | 2010/055245 | * 5/2010 |
| WO | 2010/055245 A2 | 5/2010 |

OTHER PUBLICATIONS

International Preliminary Report on Patentability received for PCT Patent Application No. PCT/US2012/047584, mailed on Feb. 6, 2014, 5 pages.
International Search Report and Written Opinion received for PCT Patent Application No. PCT/US2012/047584, mailed on Dec. 6, 2012, 5 pages.
Bailey et al., (2012) "Reaction of Grignard Reagents with Diisopropylaminoborane. Synthesis of Alkyl, Aryl, Heteroaryl and Allyl Boronic Acids from Organo(Diisopropyl)-Aminoborane by a Simple Hydrolysis", Heterocycles, 86:331-342.
Chavant et al., (1993) "Preparation of Some Organo-Bis (Diisopropylamino) Boranes and their Application to the Synthesis of Oxazaborolidines", J. Organo. Chem., 455:37-46.
Clary et al., (2011) "Facile Synthesis of Alkyl, Aryl, Heteroaryl, Vinyl and Allyl Pinacolboronate Esters: Reaction of Pinacolborane with Corresponding Halides Mediated by Magnesium under Ambient Grignard and Barbier Conditions", American Chemical Society National Meeting & Exposition, Mar. 27-31, 2011, Anaheim, Calif., 1 page.
Clary et al., (2011) "Hydride as a Leaving Group in the Reaction of Pinacolborane with Halides under Ambient Grignard and Barbier Conditions. One-Pot Synthesis of Alkyl, Aryl, Heteroaryl, Vinyl, and Allyl Pinacolboronic Esters", J. Org. Chem., 76:9602-9610.
Pintaric et al., (2010) "An Opportunity for Mg-Catalyzed Grignard-Type Reactions: Direct Coupling of Benzylic Halides with Pinacolborane with 10 Mol % of Magnesium", J. Am. Chem. Soc., 132:11825-11827.

* cited by examiner

*Primary Examiner* — Taofiq A Solola
(74) *Attorney, Agent, or Firm* — Morrison & Foerster LLP

(57) ABSTRACT

Boronic esters and boronic acids are synthesized at ambient temperature in an ethereal solvent by the reaction of Grignard reagents with a boron-containing substrate. The boron-containing substrate may be a boronic ester such as pinacolborane, neopentylglycolborane, or a dialkylaminoborane compound such as diisopropylaminoborane. The Grignard reagents may be pre-formed or generated from an alkyl, alkenyl, aryl, arylalkyl, heteroaryl, vinyl, or allyl halide compound and Mg°. When the boron-containing substrate is a boronic ester, the reactions generally proceed at room temperature without added base in about 1 to 3 hours to form a boronic ester compound. When the boron-containing substrate is a dialkylaminoborane compound, the reactions generally proceed to completion at 0° C. in about 1 hour to form a boronic acid compound.

36 Claims, 1 Drawing Sheet

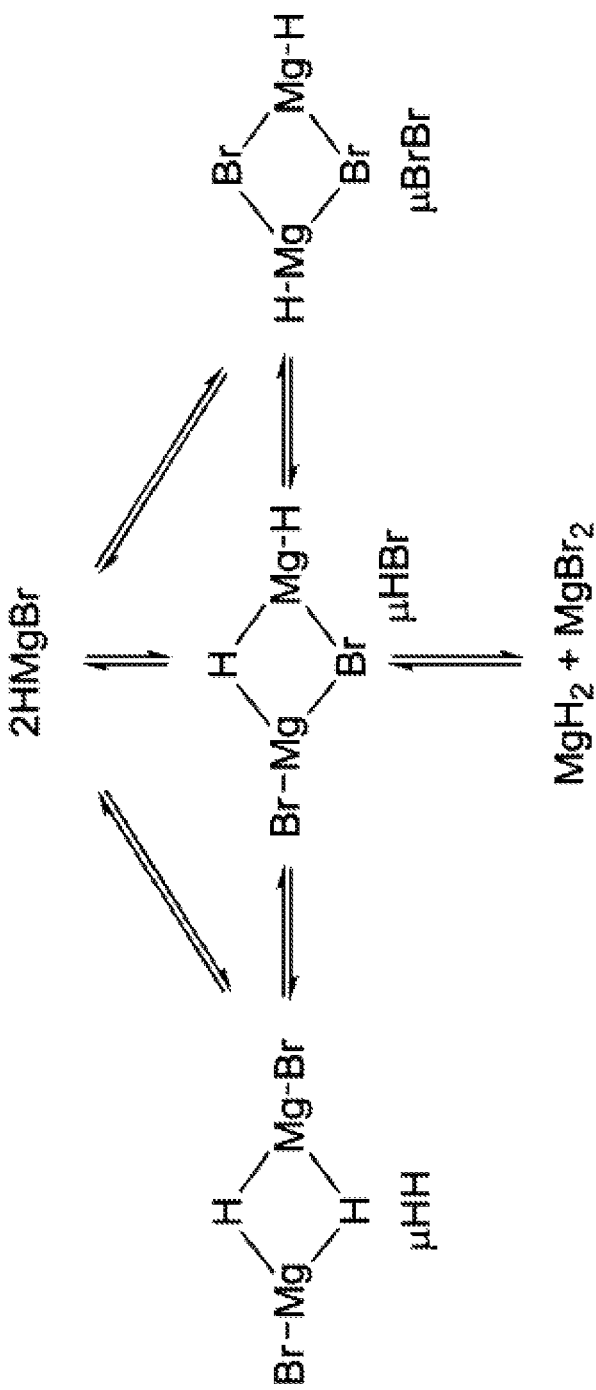

SYNTHESIS OF BORONIC ESTERS AND BORONIC ACIDS USING GRIGNARD REAGENTS

CROSS REFERENCE TO RELATED APPLICATIONS

This application is a U.S. National Phase of PCT/US2012/047584, filed Jul. 20, 2012, which claims the benefit under 35 USC 119(e) of U.S. Provisional Application No. 61/510,991, filed Jul. 22, 2011, each of which is incorporated herein by reference in its entirety for all purposes.

FIELD

The present disclosure relates generally to processes for preparing boronic esters and boronic acids. More specifically it relates to processes for preparing boronic esters and boronic acids from Grignard reagents and a suitable boron-containing substrate in a solvent.

BACKGROUND

Boronic esters and acids are widely used cross coupling reagents in medicinal and biological fields. Boronic acid based cross coupling reactions are often present in the synthesis of pharmaceuticals, agrochemical compounds, and natural products. More recent advances in cross coupling involving boronic acids include copper(II) mediated oxygen and nitrogen arylation, as well as coupling between alkenes, alkynes, carbonyl compounds, and imines. The syntheses of chiral homoallylic alcohols and amines have also been achieved through catalytic asymmetric allylboration using allylboronate esters.

Boronic acids have wide application in organic synthesis and especially in the formation of C—C bonds through the Suzuki-Miyaura cross coupling reaction. This cross coupling reaction has become ubiquitous in the construction of asymmetric biaryl systems. Because of the value of the boronic acid starting materials, great effort has been put forward to find new and more efficient methods of synthesis. Major advancements in application and versatility of the Suzuki coupling continue to increase the demand for new methods of synthesizing boronic acids and esters.

A well established method for producing arylboronic acids is the Brown-Cole transmetallation of aryllithium reagents with an excess of trialkylborate, such as trimethyl-, triethyl-, or triisopropylborate, followed by acid hydrolysis. Due to the high reactivity of lithium reagents, the reaction must be carried out at −78° C. to avoid multiple additions. Several catalytic methods have also been developed for synthesizing arylboronic acids using transition metals, such as palladium, rhodium, ruthenium, and iridium. Arylboronic esters have also been prepared through metal catalyzed C—H activation. These routes to boronic acids are widely used in industry because of their functional group tolerance. The challenges associated with these methods are the high cost of the catalytic components, catalyst decomposition, regioselectivity and non-trivial isolation of the products free of heavy metal impurities.

Several other methods for synthesizing boronic esters and acids have been developed including the Miyarua-Masuda reaction, where arylboronate esters are obtained by palladium (Pd)-catalyzed borylation of aryl halides with dialkoxyboranes or tetraalkoxydiboron reagents. These Pd catalyzed methods are tolerable to a wide range of functional groups which allows for wide application in the pharmaceutical industry. Additionally, borylation via rhodium (Rh)-catalyzed C—H activation has been developed. The drawbacks of these methods include the invariable requirement of excess boron reagent, high cost associated with the catalysts, catalyst decomposition, and the isolation of products free of heavy metal impurities.

In comparison, Grignard reagents have found limited use in the synthesis of boronic acids. Direct reaction of Grignard reagents with trialkylborates invariably gives a mixture of products arising from multiple additions. This problem could be circumvented by using excess amounts of trialkylborate. Even so, mild, low-cost synthetic processes to produce boronic acids or boronic esters are desirable.

Dunach et al. have reported synthesis of aryl and benzyl boronate esters by reacting an aryl or benzyl halide with $Mg^0$, followed by reaction with pinacolborane (WO2010/055245). However, the substrate scope was limited to aryl and benzyl groups, and the reported examples utilized stoichiometric amounts of base (e.g., triethylamine) under refluxing conditions in tetrahydrofuran for 15 h. Therefore, there remains a need for efficient reactions under mild conditions with expanded substrate scope to produce boronic esters and boronic acids.

BRIEF SUMMARY

The present disclosure relates generally to processes for preparing boronic esters and boronic acids. More specifically it relates to processes for preparing boronic esters and boronic acids from Grignard reagents and a suitable boron-containing substrate in a solvent.

In one embodiment, the present invention provides a process for preparing a boronic ester compound of formula (I):

wherein $R_1$ and $R_2$ may be joined together to form an optionally substituted ring or $R_1$ and $R_2$ are each independently selected from the group consisting of optionally substituted alkyl, optionally substituted alkenyl, optionally substituted alkynyl, optionally substituted aryl, and optionally substituted heteroaryl;

and wherein $R_3$ is selected from the group consisting of optionally substituted alkyl, optionally substituted alkenyl, and optionally substituted allyl;

the process comprising combining a Grignard reagent with $BH(OR_1)(OR_2)$ in a solvent to form the boronic ester compound of formula (I). In some embodiments, the $BH(OR_1)(OR_2)$ is selected from the group consisting of pinacolborane, catecholborane, neopentylglycolborane, and mixtures thereof. In other embodiments, the $BH(OR_1)(OR_2)$ is selected from the group consisting of pinacolborane, neopentylglycolborane, and mixtures thereof. In other embodiments, the $BH(OR_1)(OR_2)$ is neopentylglycolborane. In some embodiments, $R_3$ is optionally substituted alkyl. In other embodiments, $R_3$ is optionally substituted C1-C10 alkyl or optionally substituted C4-C8 cycloalkyl. In other embodiments, $R_3$ is selected from the group consisting of methyl, ethyl, n-propyl, isopropyl, n-butyl, iso-butyl, sec-butyl, tert-butyl, n-pentyl, n-hexyl, n-heptyl, n-octyl, n-nonyl, n-decyl, cyclopentyl, cyclohexyl, cycloheptyl, and cyclooctyl. In some embodiments, $R_3$ is optionally substituted alkenyl. In other embodiments, $R_3$ is optionally substituted C2-C10 alkenyl or optionally substituted C4-C8 cycloalkenyl. In other embodiments, $R_3$ is selected from the group consisting of vinyl, α-vinylbenzene, pentenyl, hexenyl, heptenyl, octenyl, nonenyl, decenyl, cyclohexenyl, cycloheptenyl, and cyclooctenyl. In some embodiments where $R_3$ is optionally substituted alkyl or alkenyl, the Grignard reagent is generated from an $R_3$-halide compound and $Mg^0$. In other embodiments where $R_3$ is optionally substituted alkyl or alkenyl, about 1.2 equivalents of $Mg^0$, about 1.0 equivalents of $R_3$-halide, and about 1.0 equivalents of $BH(OR_1)(OR_2)$ are combined to form the boronic ester compound of formula (I). In some embodiments, $R_3$ is optionally substituted allyl. In other embodiments, $R_3$ is optionally substituted C3-C6 allyl. In other embodiments, the compound of formula (I) is selected from the group consisting of:

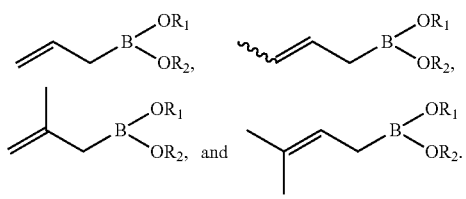

In some embodiments where $R_3$ is optionally substituted allyl, the Grignard reagent is generated from an $R_3$-halide compound and $Mg^0$. In other embodiments where $R_3$ is optionally substituted allyl, about 1.2 equivalents of the $Mg^0$, about 2.0 equivalents of the $R_3$-halide, and about 1.0 equivalents of the $BH(OR_1)(OR_2)$ are combined to form the boronic ester compound of formula (I). In some embodiments, the process to prepare a boronic ester compound of formula (I) produces a HMgX intermediate, wherein X is either chloro or bromo, and wherein the HMgX intermediate disproportionates to form a $MgH_2$ byproduct. In other embodiments, the HMgX intermediate acts as a leaving group prior to formation of the $MgH_2$ byproduct. In some embodiments, the process to prepare a boronic ester compound of formula (I) further generates a $MgX_2$ byproduct, wherein X is either chloro or bromo. In other embodiments, X is bromo. In some embodiments, the process for preparing the boronic ester compound of formula (I) proceeds at a temperature of about 0° C. to about 50° C. In other embodiments, the temperature of the process is about 20° C. to about 30° C. In other embodiments, the temperature of the process is about 22-27° C. In some embodiments, the temperature of the process is about ambient temperature. In some embodiments, the process for preparing the boronic ester compound of formula (I) takes about 15 minutes to about 12 hours. In other embodiments, the process takes about 15 minutes to about 5 hours. In other embodiments, the process takes about 15 minutes to about 3 hours. In some embodiments, the Grignard reagent adds one $R_3$ group to $BH(OR_1)(OR_2)$ to produce the boronic ester compound of formula (I). In other embodiments, the process is carried out in the absence of a base. In other embodiments, the solvent is an ethereal solvent. In other embodiments, the solvent is tetrahydrofuran. In some embodiments, the process further comprises hydrolyzing the boronic ester compound to form a boronic acid compound.

In one embodiment, the present invention provides a process for preparing a boronic acid compound of formula (II):

wherein $R_4$ is selected from the group consisting of optionally substituted alkyl, optionally substituted alkenyl, optionally substituted allyl, optionally substituted aryl, optionally substituted arylalkyl, and optionally substituted heteroaryl;

the process comprising combining a Grignard reagent with an optionally substituted dialkylaminoborane in a solvent to form the boronic acid compound of formula (II). In some embodiments, $R_4$ is selected from the group consisting of optionally substituted aryl, optionally substituted arylalkyl, and optionally substituted heteroaryl. In other embodiments, $R_4$ is optionally substituted aryl. In other embodiments, the compound of formula (II) is selected from the group consisting of:

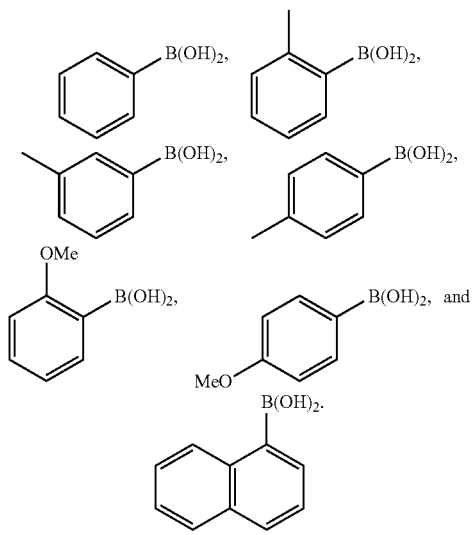

In some embodiments, $R_4$ is optionally substituted allyl. In other embodiments, $R_4$ is selected from the group consisting of allyl, but-2-enyl, 2-methylallyl, and 3-methylbut-2-enyl. In some embodiments, $R_4$ is optionally substituted alkyl. In other embodiments, $R_4$ is optionally substituted C1-C10 alkyl or optionally substituted C4-C8 cycloalkyl. In other embodiments, $R_4$ is selected from the group consisting of methyl, ethyl, n-propyl, isopropyl, n-butyl, iso-butyl, sec-butyl, tert-butyl, n-pentyl, n-hexyl, n-heptyl, n-octyl, n-nonyl, n-decyl, cyclopentyl, cyclohexyl, cycloheptyl, and cyclooctyl. In some embodiments, $R_4$ is optionally substituted heteroaryl. In other embodiments, $R_4$ is selected from the group consisting of furanyl and thiophene. In other embodiments, $R_4$ is thiophene. In some embodiments, the process for preparing a boronic acid compound of formula (II) proceeds at a temperature of about −78° C. to about 25° C. In other embodiments, the temperature of the process is about −50° C. to about 10° C. In other embodiments, the temperature of the process is about −30° C. to about 5° C. In other embodiments, the temperature of the process is about 0° C. In some embodiments, the process for preparing a boronic acid compound of formula (II) includes generating the Grignard reagent from an $R_4$-halide compound and $Mg^0$. In some embodiments, the process for preparing a boronic acid compound of formula (II) takes about 1 hour to about 12 hours. In some embodiments, the process takes about 1 hour to about 5 hours. In some embodiments, the process takes about 1 hour to about 3 hours. In some embodiments, the Grignard reagent adds one $R_4$ group to the dialkylaminoborane to produce a $R_4$-dialkylaminoborane adduct. In other embodiments, the $R_4$-dialkylaminoborane adduct is hydrolyzed to form the boronic acid compound of formula (II). In some embodiments, the optionally substituted dialkylaminoborane is diisopropylaminoborane. In some embodiments, the solvent used in preparing a boronic acid compound of formula (II) is an ethereal solvent. In other embodiments, the solvent is tetrahydrofuran.

BRIEF DESCRIPTION OF THE DRAWINGS

FIG. 1 illustrates the μHBr-bridged HMgBr dimer as a possible intermediate in the formation of $MgH_2$ and $MgBr_2$. $MgH_2$ and $MgBr_2$ are generated in the reaction of a Grignard reagent with pinacolborane.

DETAILED DESCRIPTION

The following description sets forth exemplary methods, parameters and the like. It should be recognized, however, that such description is not intended as a limitation on the scope of the present disclosure but is instead provided as a description of exemplary embodiments.

1. DEFINITIONS

As used herein, the term "about" means approximately, in the region of, roughly, or around. When the term "about" is used in conjunction with a numerical range, it modifies that range by extending the boundaries above and below the numerical values set forth. The term "about" is used herein to modify a numerical value above and below the stated value by a variance of ±10%.

As used herein, the terms "alkyl," "alkenyl," and "alkynyl" include straight-chain, branched-chain, and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl, and alkynyl substituents of the disclosure contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond. Where an alkenyl substituent is recited such as "pentenyl" or "hexenyl," the substituent alkenyl double bond may be in any possible position and the point of attachment of the substituent may be any carbon atom.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C3-C8 heterocyclyl, C4-C10 heterocyclylalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C8 alkyl, C2-C8 heteroalkyl, C3-C8 heterocyclyl, C4-C10 heterocyclylalkyl, C1-C8 acyl, C2-C8 heteroacyl, C6-C10 aryl or C5-C10 heteroaryl. Alkyl, alkenyl, and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R or R' groups on the same or adjacent atoms (e.g., $-NR_2$, or —NR—C(O)R), the two R or R' groups can optionally be taken together with the atoms in the substituent group to which they are attached to form a ring having 5-8 ring members, which can be substituted as allowed for the R or R' itself, and can contain an additional heteroatom (N, O or S) as a ring member.

"Heteroalkyl," "heteroalkenyl," and "heteroalkynyl" and the like are defined similarly to the corresponding hydrocarbyl (alkyl, alkenyl, and alkynyl) groups, but the 'hetero' terms refer to groups that contain 1-3 O, S or N heteroatoms or combinations thereof within the backbone residue; thus, at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O, and S. Thus heteroacyl includes, for example, —C(=O)OR and —C(=O)NR$_2$ as well as —C(=O)— heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Typically, the substituent contains at least one aromatic ring that does not have a heteroatom as a ring member, whereas "heteroaromatic" or "heteroaryl" refers to an aromatic group containing at least one heteroatom as a ring member. The aryl and heteroaryl structures encompass compounds having monocyclic, bicyclic, or multiple ring systems, and thus they may include a mixture of aryl and heteroaryl groups provided that where the group is referred to as 'aryl' it is attached to the molecule at a position of an aryl ring of the 'aryl' group, and where it is described as 'heteroaryl' it is attached to the molecule at a position of a heteroaryl ring of the group. These groups may be single (isolated) rings or they may be ring systems including multiple fused rings; thus aryl groups can include an indole, benzofuran or tetrahydronaphthyl group, for example, provided that the point of attachment is on a ring that is an aryl ring.

Similarly, "heteroaromatic" and "heteroaryl" refer to such monocyclic or fused bicyclic ring systems that contain as ring members one or more heteroatoms selected from O, S, and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system that has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C3-C8 cycloalkyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and each R is optionally substituted as described above for alkyl groups. Where a substituent group contains two R or R' groups on the same or adjacent atoms (e.g., —NR$_2$, or —NR—C(O)R), the two R or R' groups can optionally be taken together with the atoms in the substituent group to which the are attached to form a ring having 5-8 ring members, which can be substituted as allowed for the R or R' itself, and can contain an additional heteroatom (N, O, or S) as a ring member. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems that are bonded to their attachment point through a linking group such as an alkylene, including substituted or unsubstituted, saturated or unsaturated, or cyclic or acyclic linkers. Typically the linker is C1-C8 alkyl or a heteroform thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O, and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$— may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl, or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the disclosure, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O, and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O, or S atoms are ordinarily connected sequentially, except where an oxo group is attached to N or S to form a nitro or sulfonyl group.

"Halo" or "halide" as used herein includes fluoro, chloro, bromo, and iodo. Preferred halo or halide substituents include chloro and bromo.

"Optionally substituted" as used herein means the same as the term "substituted or unsubstituted" and the terms may be used interchangeably. "Optionally substituted" indicates that the particular group or groups being described may have no non-hydrogen substituents ("unsubstituted"), or the group or groups may have one or more non-hydrogen substituents ("substituted"). For example, an "optionally substituted alkyl" includes "substituted or unsubstituted alkyl" groups such as —$CH_2F$ ("substituted") or —$CH_3$ ("unsubstituted"). If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

2. DESCRIPTION

The present disclosure is directed to reactions of Grignard reagents with atypical boron donors (e.g., other than trialkylborates), such as 4,4,5,5-tetramethyl-1,3,2-dioxaborolane (pinacolborane, PinBH). Pinacolboronate esters are known to be oxidatively and hydrolytically very stable compared to boronic acids. Their added stability and compatability as coupling partners in the Suzuki-Miyaura cross-coupling reaction makes pinacolboronate esters synthetically valuable targets. Pinacolborane is commercially available and it may be synthesized by the mixing of equal molar amounts of borane-tetrahydrofuran (THF), borane-methyl sulfide complex or borane-amine complex and pinacol. Allylpinacolboronate esters may be preferred to allylboronic acids for catalytic asymmetric allylboration reactions since allylpinacolboronate esters do not give background achiral allylboration. On the other hand, boronic acids have a lower molecular weight and therefore may be preferred based on atom economy.

The present disclosure provides processes for preparing boronic esters and boronic acids from Grignard reagents and a suitable boron-containing substrate in a solvent. For the production of boronic acids or boronic esters, the boron-containing substrate may be $BH(OR_1)(OR_2)$, wherein $R_1$ and $R_2$ may be joined together to form an optionally substituted ring or $R_1$ and $R_2$ are each independently selected from the group consisting of hydrogen, optionally substituted alkyl, optionally substituted alkenyl, optionally substituted alkynyl, optionally substituted aryl, and optionally substituted heteroaryl. For the preparation of boronic acids, the boron-containing substrate may be an optionally substituted diialkylaminoborane, such as, for example, diisopropylaminoborane.

The present disclosure provides processes that are mild, simple, and highly efficient for synthesizing pinacolboronate esters utilizing environmentally friendly Grignard reagents and PinBH. In some embodiments, freshly prepared Grignard reagents react with PinBH in THF at 25° C. affording a variety of boronate esters in excellent isolated yield. In other embodiments, under Barbier conditions aryl, vinyl, benzyl, and allylic halides are converted to the corresponding boronate esters essentially quantitatively. Performing the borylation reaction under Barbier conditions avoids Wurtz coupling byproducts as well as allowing use of a simple one pot procedure for the synthesis of allylboronates from allyl bromides. Boronate ester synthesis by the processes disclosed herein avoids the use of low temperatures and toxic transition metal catalysts. In some embodiments, neopentylglycolborane, another cyclic dialkoxyborane, may be used to synthesize boronate esters or acids. None of the processes disclosed herein require a stoichiometric amount of a base such as triethylamine. Use of a base such as triethylamine gives essentially quantitative yield of the corresponding quaternary salt from aliphatic, allylic and benzylic halides. The processes disclosed herein proceed rapidly at ambient temperature and produce the product boronate esters and the byproduct HMgX.

The processes disclosed herein allow for the synthesis of optionally substituted allyl compounds such as allyl, methallyl, and prenyl pinacolboronates without any Wurtz coupling side products under Barbier conditions at room temperature from optionally substituted allyl halide substrates. Optionally substituted allyl halide substrates may be more difficult than aryl or benzyl halide substrates as they may be more easily reduced under the reaction conditions. Additionally, the processes disclosed herein allow for the synthesis of optionally substituted alkyl boronate esters from alkyl halides. Alkyl halides may be more difficult substrates than aryl or benzyl halide substrates as alkyl groups do not have the ability to stabilize intermediates by resonance stabilization. Furthermore, alkyl, allyl, and methallyl halides may be more difficult substrates than aryl or benzyl halide substrates due to steric and/or electronic differences.

Boronic Ester and Boronic Acid Synthesis from Grignard Reagents and $BH(OR_1)(OR_2)$.

The present disclosure provides processes for the synthesis of boronic esters from Grignard Reagents and $BH(OR_1)(OR_2)$ according to the following exemplary reaction:

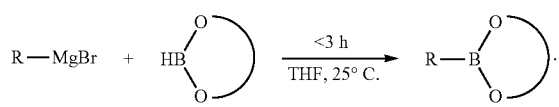

The boronic esters may be further hydrolyzed to form boronic acids.

In some embodiments, the processes described herein produce a boronic ester compound of formula (I):

wherein $R_1$ and $R_2$ may be joined together to form an optionally substituted ring or $R_1$ and $R_2$ are each independently selected from the group consisting of optionally substituted alkyl, optionally substituted alkenyl, optionally substituted alkynyl, optionally substituted aryl, and optionally substituted heteroaryl;

and wherein $R_3$ is selected from the group consisting of optionally substituted aryl, optionally substituted arylalkyl, optionally substituted heteroaryl, optionally substituted alkyl, optionally substituted alkenyl, and optionally substituted allyl. Preferred $R_3$ substituents include optionally substituted alkyl, optionally substituted alkenyl, and optionally substituted allyl. In some embodiments, the substrate may incorporate a masked carbonyl group, such as, for example, an acetal that may be deprotected under acidic conditions to yield an aldehyde.

The boronic ester compound of formula (I) may be further hydrolyzed to form the corresponding boronic acid compound.

Processes that produce the boronic ester compound of formula (I) typically involve combining a Grignard reagent with $BH(OR_1)(OR_2)$ in a solvent. The Grignard reagent may be preformed (e.g., commercially available) or may be generated in situ by the reaction of a $R_3$-halide compound and $Mg^0$ under Barbier-type conditions. A wide variety of Grignard reagents may be accommodated in the reaction in quantitative yields (See Example 1, Table 1). The $Mg^0$ (magnesium metal) used may be in a variety of forms, such as, for example, a bar, powder, turnings, pieces, or other forms. The $Mg^0$ may be coated with a passivating layer of $Mg^0$, which may be weakened by adding a small amount of an activating agent. Non-limiting examples of such activating agents include iodine, methyl iodide, 1,2-dibromoethane, and mercuric chloride.

Non-limiting examples of the $BH(OR_1)(OR_2)$ substrate include pinacolborane, catecholborane, and neopentylglycolborane. Neopentylglycolborane may be preferred over pinacolborane from a cost perspective, but both boranes produce the boronic ester compounds in high yields. In some preferred embodiments, freshly prepared Grignard reagents and pure $BH(OR_1)(OR_2)$ are used instead of solutions of $BH(OR_1)(OR_2)$ because a $BH(OR_1)(OR_2)$ solution in tetrahydrofuran may degrade significantly at 25° C. over a few days. However, neat PinBH (97%) was stable at 25° C. for at least seven months. The main disproportionation product is trispinacolborane ($B_2Pin_3$, +21 ppm, s). Trispinacolborane will undergo multiple additions when reacted with a Grignard reagent.

The solvent used in the reaction to prepare the boronic ester compound of formula (I) typically is an ethereal solvent. Non-limiting examples of ethereal solvents include dimethyl ether, diethyl ether, dimethoxyethane, tetrahydrofuran, tetrahydropyran, dioxane, and anisole. In some preferred embodiments, the solvent used is tetrahydrofuran.

The processes to prepare the boronic ester compound of formula (I) are typically conducted at ambient temperature without the need of additional heat or refluxing. In some embodiments, the temperature of the process is about 25° C. In other embodiments, the temperature of the process ranges from about 20° C. to about 30° C. In some embodiments, the temperature of the process ranges from about 0° C. to about 50° C. Generally, the reactions are completed in short reaction times. In some embodiments, the reaction time ranges from about 15 minutes to about 12 hours. In some embodiments, the reaction time ranges from about 15 minutes to about 5 hours. In some preferred embodiments, the reaction time ranges from about 15 minutes to about 3 hours. In some embodiments, aryl Grignard reagents completely react with $BH(OR_1)(OR_2)$ within 1 hour. In some embodiments, alkyl Grignard reagents completely react with $BH(OR_1)(OR_2)$ within 30 minutes.

Typically, the processes to prepare the boronic ester compound of formula (I) are carried out without the addition of a base. In some embodiments, the reaction of $BH(OR_1)(OR_2)$ and optionally substituted alkylmagnesium bromide Grignard reagents produces a precipitate, sometimes in minutes. In other embodiments, the reaction of $BH(OR_1)(OR_2)$ and optionally substituted alkylmagnesium chloride, arylmagnesium bromide, and arylmagnesium chloride Grignard reagents do not produce any precipitate until the addition of a hydrocarbon solvent such as pentanes or hexanes. Typically, the reactions proceed without any observable gas evolution. Generally, no Wurtz coupling byproducts are observed in the reaction.

Under Barbier-type conditions and in the absence of a base, a variety of aryl halides are smoothly converted to the corresponding boronate esters in high yields (See Example 3 and Table 2). The process is compatible with masked carbonyl groups such as acetal. For example, p-benzaldehyde dimethyl acetal boronate ester (See Table 2, entry 6) was isolated in 87% yield. The compound can be deprotected under acidic conditions to yield the p-benzaldehydeboronate ester. Benzyl boronate ester was synthesized under these conditions but required a stoichiometric amount of $Mg^0$. In some embodiments, the processes form heterocyclic boronate esters (See Table 2, Entries 10 and 11). Vinyl boronic esters may also be synthesized under Barbier conditions.

In some embodiments, when $R_3$ is optionally substituted alkyl or alkenyl, and the Grignard reagent is generated from an $R_3$-halide compound and $Mg^0$, the reagents are combined using about 1.2 equivalents of $Mg^0$, about 1.0 equivalents of $R_3$-halide, and about 1.0 equivalents of $BH(OR_1)(OR_2)$ to form the boronic ester compound of formula (I).

In some embodiments, when $R_3$ is optionally substituted allyl, and the Grignard reagent is generated from an $R_3$-halide compound and $Mg^0$, the reagents are combined using about 1.2 equivalents of $Mg^0$, about 2.0 equivalents of $R_3$-halide, and about 1.0 equivalents of $BH(OR_1)(OR_2)$ to form the boronic ester compound of formula (I).

When allylbromide was used under the Barbier conditions described above, $^{11}B$ NMR analysis showed approximately a 1:1 mixture of the corresponding allylboronate and unreacted PinBH. Additionally, approximately 50% of the $Mg^0$ remained unreacted even after extended periods of reaction time. Competitive Wurtz coupling due to the high reactivity of allylbromide reagents towards homocoupling may consume the starting material, but $^1H$ NMR analysis of the product mixture showed no Wurtz coupling products or allylbromide starting material. Without bound by any theory, we then speculated the HMgBr byproduct was reducing the unreacted allylbromide, which would account for the 1:1 mixture of allylboronate and PinBH observed in the $^{11}B$ NMR spectra. This problem was circumvented by the addition of a second equivalent of allylbromide. Thus, the synthesis of allylpinacolboronate esters (PinBAll) requires a stoichiometric amount of magnesium metal and portion-wise addition of two equivalents of allyl bromide for quantitative yield (Table 3). When benzylbromide and allylbromide were reacted under the recently reported catalytic condition only 10% of the corresponding boronate esters were isolated along with essentially quantitative amounts of the corresponding quaternary salts. The processes reported herein allow for the synthesis of allyl and methallyl boronate esters from magnesium under Barbier condition at room temperature. Otherwise, one has to either buy allyl and methallyl boronate esters from a commercial source or make it by reaction of pinacol with pyrophoric triallylborane.

The boronic ester compounds of formula (I) that are generated in the reaction may be isolated using a variety of techniques known in the art. For example, $R_3$—$B(OR_1)(OR_2)$ compounds may be isolated from magnesium hydrides by quenching the reaction mixture with an acid such as hydrochloric acid (1 M) followed by extraction with an organic solvent such as diethyl ether. Alternatively, saturated aqueous ammonium chloride may be added followed by extraction with an organic solvent such as diethyl ether.

The reaction between diakoxyboranes and a Grignard reagent may be studied by $^{11}B$ NMR spectroscopy. For example, the reaction between dialkoxyboranes and p-tolylmagnesium bromide (p-tolylMgBr) was followed by $^{11}B$ NMR spectroscopy. Grignard reagents reacted with acyclic dialkoxyboranes, such as diisopropoxyborane, at 25° C. to yield a mixture of products due to multiple additions to the boron donor. However, cyclic dialkyoxyboranes react readily with Grignard reagents. For example, p-tolylMgBr reacted readily with the cyclic dialkoxyborane, PinBH, to give exclusively a monoaddition product. Analogous reactions between PinBH and alkyl lithium reagents and triorganylsilyl lithium reagents are known in the art. However, these reactions are not general for alkyl and aryl lithium reagents and we found phenyl lithium gives multiple addition products with PinBH, even at low temperature. In comparison, aryl Grignard reagents give exclusively a monoaddition product with PinBH. Without being bound by any theory, the arylpinacolboronates may be sterically demanding enough to prevent multiple additions to the boron center.

Functional groups in the boronate esters prepared are not tolerated due to an inherent limitation of any boronate synthesis involving Grignard reagents. Knochel's functionalized Grignard was attempted, but the lithium salts present in Knochel's Grignard synthesis ring-opened the PinBH and caused multiple additions under the reaction conditions.

Boronic Acid Synthesis from Grignard Reagents and Optionally Substituted Dialkylaminoboranes.

In some embodiments of the processes disclosed herein, optionally substituted dialkylaminoboranes such as diisopropylaminoborane are employed. The dialkylaminoboranes are inexpensive, stable over long periods of storage, and compatible with Grignard reagents for the synthesis of boronic acids. The direct reaction of Grignard reagents with diisopropylaminoborane resulted as the continuation of several previous studies of this substrate relating to the development of lithium aminoborohydride (LAB) reagents by Singaram. LAB reagents are extremely powerful reductants capable of reducing esters, lactones, and anhydrides to the corresponding alcohols, while carboxylic acids are not reduced. In addition, LAB reagents can reduce a wide range of functional groups, including amides, epoxides, oximes, nitriles, and halides.

The present disclosure provides processes for the synthesis of boronic acids from Grignard Reagents and an optionally substituted dialkylaminoborane according to the following exemplary reaction:

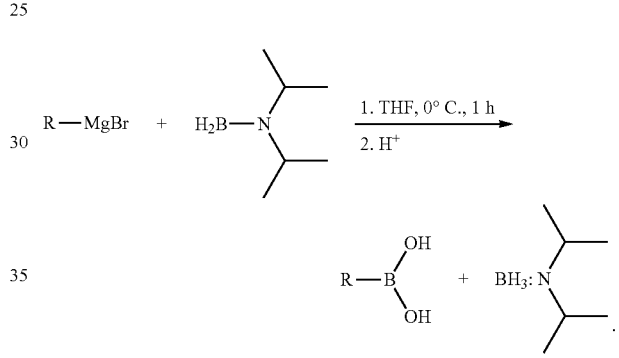

In some embodiments, the processes described herein produce boronic acid compounds of formula (II):

wherein $R_4$ is selected from the group consisting of optionally substituted alkyl, optionally substituted alkenyl, optionally substituted allyl, optionally substituted aryl, optionally substituted arylalkyl, and optionally substituted heteroaryl;

Processes that produce compounds of formula (II) involve combining a Grignard reagent with a dialkylaminoborane in a solvent. The Grignard reagent may be preformed (e.g., commercially available) or may be generated in situ by the reaction of a $R_3$-halide compound and $Mg^0$ (Barbier conditions). The $Mg^0$ (magnesium metal) used may be in a variety of forms, such as, for example, a bar, powder, turnings, pieces, or other forms. The $Mg^0$ may be coated with a passivating layer of MgO, which may be weakened by adding a small amount of an activating agent. Non-limiting examples of such activating agents include iodine, methyl iodide, 1,2-dibromoethane, and mercuric chloride. In some embodiments, the dialkylaminoborane is diisopropylaminoborane. Dialkylaminoborane compounds may be synthesized by known procedures such as reacting boran/dimethylsulfide complex (BMS) and a dialkylamine in the presence of n-butyl lithium to produce a lithium aminoborohydride compound. The lithium aminoborohydride compound may be then reacted with trimethylsilyl chloride (TMSCl) to produce the optionally substituted dialkylaminoborane compound.

The solvent used in the reaction to prepare compounds of formula (II) typically is an ethereal solvent. Non-limiting examples of ethereal solvents include dimethyl ether, diethyl ether, dimethoxyethane, tetrahydrofuran, tetrahydropyran, dioxane, and anisole. In some preferred embodiments, the solvent used is tetrahydrofuran.

The processes to prepare compounds of formula (II) are typically conducted at temperatures at or below ambient temperature. In some embodiments, the temperature of the process is about 0° C. In other embodiments, the temperature of the process ranges from about −78° C. to about 25° C. In some embodiments, the temperature of the process ranges from about −50° C. to about 10° C. In some embodiments, the temperature of the process ranges from about −30° C. to about 5° C. Generally, the reactions are completed in short reaction times. In some embodiments, the reaction time ranges from about 1 hour to about 12 hours. In some embodiments, the reaction time ranges from about 1 hour to about 5 hours. In some preferred embodiments, the reaction time ranges from about 1 hour to about 3 hours. Generally, no Wurtz coupling byproducts are observed in the reaction.

The boronic acid compounds of formula (II) that are generated in the reaction may be isolated using a variety of techniques known in the art. For example, $R_4$—$B(OH)_2$ compounds may be isolated from magnesium hydrides by quenching the reaction mixture with an acid at such as hydrochloric acid (1 M) at about 0° C. followed by a reflux from about 5 minutes to about 30 minutes. In some preferred embodiments, the reflux time is about 15 minutes. Following the reflux, the compound of formula (II) may be extracted in an organic solvent, such as, for example, diethyl ether.

EXAMPLES

The following non-limiting examples are provided to further illustrate the present disclosure.

Abbreviations: MHz (megahertz); NMR (nuclear magnetic resonance); PinBH (4,4,5,5-tetramethyl-1,3,2-dioxaborolane, also known as pinacolborane); and THF (tetrahydrofuran).

All reactions were performed in oven-dried, argon-cooled glassware. The pinacolborane was used as received from Aldrich, stored under argon in a refrigerator held at 15° C. All Grignard reagents were used as received from Aldrich, they were stored in the bottle received and kept in the refrigerator held at 15° C. All air and moisture-sensitive compounds were introduced via syringes or cannula through a rubber septum. Pinacolborane was added via syringe, with dispensed amount measured by mass difference of the syringe before and after addition. Tetrahydrofuran (THF) was freshly obtained from a solvent purification system or distilled from sodium-benzophenone. NMR spectra were recorded in $CDCl_3$. Chemical shifts are reported relative to TMS ($\delta$=0) for $^1H$ NMR and are referenced to the $CDCl_3$ resonance ($\delta$=77) for $^{13}C$ NMR spectra. Boron NMR samples were recorded at 160.4 MHz and are reported relative to external standard $BF_3:Et_2O$ ($\delta$=0). $^{11}B$-NMR spectroscopy may be used to monitor the processes described herein to provide insights into potential reaction mechanisms as well as potential intermediates and byproducts that are formed during the process. However, one of skill in the art will recognize that proposed mechanisms may not actually be operable in the processes described herein, and other alternatives may be possible.

Example 1

Preparation of Aryl and Alkyl-Pinacolboronate Esters Using Preformed Grignard Reagents The following procedure for the preparation of m-tolyl pinacolborane is representative. A 25-mL round-bottom flask equipped with a magnetic stir bar and fitted with rubber septum was charged with anhydrous THF (4.0 mL) followed by pinacolborane (0.57 g, 4.5 mmol). m-Tolylmagnesium bromide (4.5 mmol, 1 M/THF) was added dropwise over 5 min. at 25° C. with constant stirring. The reaction was complete after 1 h as evidenced by the disappearance of pinacolborane starting material ($\delta$ +27.7, d, J=173.9 Hz), and the appearance of a singlet at +30.5 ppm via $^{11}B$-NMR. The reaction was then cooled to 0° C. (ice bath) and acidified with 3 M aqueous HCl (3 mL) (CAUTION: hydrogen evolution). After 10 min of stirring the reaction mixture was warmed to 25° C. and stirred for an additional 30 min. The reaction mixture was then transferred to a separatory funnel and extracted with diethyl ether (3×15 mL). The combined organic layers were dried over anhydrous $MgSO_4$, filtered, and dried under vacuo (25° C., 1 Torr) to afford m-tolyl pinacolborane as a pale yellow oil. The results for the other pinacolborane esters prepared by this method are summarized in Table 1. Table 1, Entry 6 had an isolated yield of 85% after flash column chromatography (hexane/ethyl acetate, 30/1).

TABLE 1

Synthesis of Aryl and Alkyl Boronate Esters using Grignard Reagents[a]

| Entry | Product | Isolated Yield (%) |
|---|---|---|
| 1 | 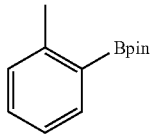 Bpin | 90[b] |
| 2 | Bpin | 80 |
| 3 | 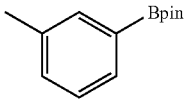 Bpin | 90 |

TABLE 1-continued

Synthesis of Aryl and Alkyl Boronate Esters using Grignard Reagents[a]

R3—MgBr + HB(pin) →(1. THF, 25° C., 1 h; 2. HCl)→ R3—Bpin

| Entry | Product | Isolated Yield (%) |
|---|---|---|
| 4 | p-Tolyl-Bpin | 89 |
| 5 | 4-MeO-C6H4-Bpin | 70 |
| 6 | 9-Phenanthryl-Bpin | 92 |
| 7 | n-Hexyl-Bpin | 90 |
| 8 | Cyclohexyl-Bpin | 82 |
| 9 | t-Bu-Bpin | 65 |
| 10 | 3-Pentyl-BPin | 99 |

[a]Reagents and conditions: PinBH (4.5 mmol), anhydrous THF (4.0 mL), Grignard reagent (4.5 mmol), argon, 25° C., 1 h.
[b]required 2 eq of PinBH and reaction temperature of 0° C.

Phenylboronic acid pinacolester (Table 1, entry 1). The spectroscopic data match those reported previously (*J. Am. Chem. Soc.* 2002, 124, 390-391). This compound required 2 eq of PinBH and reaction temperature of 0° C. Colorless oil; 96% yield (0.598 g). $^1$H NMR (500 MHz, CDCl$_3$) δ 1.36 (s, 12H), 7.38 (m, 2H), 7.47 (m, 1H), 7.83 (d, J=7.2 Hz, 2H); $^{13}$C NMR (125.7 MHz, CDCl$_3$): δ 25.06, 83.88, 127.91, 131.46, 134.97; $^{11}$B NMR (160.4 MHz, CDCl$_3$): δ +30.8 (s).

o-Tolylboronic acid pinacolester (Table 1, entry 2); The spectroscopic data match those reported previously (*J. Org. Chem.* 2000, 65, 164-168). Colorless oil; 80% yield (0.865 g). $^1$H NMR (500 MHz, CDCl$_3$): δ 1.43 (s, 12H), 2.65 (s, 3H), 7.24-7.26 (m, 2H), 7.41 (t, J=8, 1H), 7.89 (d, J=7, 1H). $^{13}$C NMR (125.7 MHz, CDCl$_3$): δ 25.11, 83.60, 125.10, 130.17, 131.11, 136.45, 145.19; $^{11}$B NMR (160.4 MHz, CDCl$_3$): δ +32.0 (s).

m-Tolylboronic acid pinacolester (Table 1, entry 3); The spectroscopic data match those reported previously (*J. Am. Chem. Soc.* 2000, 122, 12868-12869). Colorless oil; 78% yield (0.855 g). $^1$H NMR (500 MHz, CDCl$_3$): δ 1.36 (s, 12H), 2.37 (s, 3H), 7.28-7.29 (m, 2H), 7.62-7.63 (m, 1H), 7.65 (s, 1H). $^{13}$C NMR (125.7 MHz, CDCl$_3$): δ 24.93, 83.83, 124.43, 127.86, 131.95, 132.20, 135.52, 137.31. $^{11}$B NMR (160.4 MHz, CDCl$_3$): δ +30.3 (s).

p-Tolylboronic acid pinacolester (Table 1, entry 4); The spectroscopic data match those reported previously (*J. Org. Chem.* 2000, 65, 164-168). Colorless/yellow oil; 89% yield (0.579 g). $^1$H NMR (500 MHz, CDCl$_3$): δ 1.46 (s, 12H), 2.48 (s, 3H), 7.32 (d, J=2.4, 2H), 7.89 (d, J=2.6 Hz, 2H); $^{13}$C NMR (125.7 MHz, CDCl$_3$): δ 21.86, 25.00, 83.79, 128.79, 128.88, 135.17, 141.59; $^{11}$B NMR (160.4 MHz, CDCl$_3$): δ +31.6 (s).

4-methoxyboronic acid pinacolester (Table 1, entry 5); The spectroscopic data match those reported previously (*J. Org. Chem.* 2000, 65, 164-168). Colorless oil; 70% yield (0.804 g). $^1$H NMR (500 MHz, CDCl$_3$): 1.35 (s, 12H), 3.84 (s, 3H), 6.91 (d, J=8.5 Hz, 2H), 7.77 (d, J=8.5 Hz, 2H); $^{13}$C NMR (125.7 MHz, CDCl$_3$): δ 25.05, 55.29, 83.74, 113.50, 136.71, 160.20; $^{11}$B NMR (160.4 MHz, CDCl$_3$): δ +29.6 (s).

Phenanthrylboronic acid pinacolester (Table 1, entry 6); The spectroscopic data match those reported previously (*J. Am. Chem. Soc.* 2005, 127, 14263-14278). Colorless oil; 92% yield (1.488 g). $^1$H NMR (500 MHz, CDCl$_3$): δ 1.47 (s, 12H), 7.58-7.71 (m, 3H), 7.76 (s, 1H), 7.93 (dd, J=8.0, 20 Hz, 1H), 8.40 (s, 1H), 8.68-8.72 (m, 2H), 8.83-8.85 (m, 1H); $^{13}$C NMR (125.7 MHz, CDCl$_3$): δ 25.19, 84.07, 122.69, 122.83, 126.35, 126.65, 126.77, 126.83, 126.93, 127.11, 127.95, 128.77, 129.32, 129.55, 130.12, 131.21, 132.11, 134.69, 138.35; $^{11}$B NMR (160.4 MHz, CDCl$_3$): δ +31.3 (s).

n-Hexylboronic acid pinacolester (Table 1, entry 7); The spectroscopic data match those reported previously (*J. Org. Chem.* 1986, 51, 337-342). Colorless oil; 90% yield (0.941 g). $^1$H NMR (500 MHz, CDCl$_3$): δ 0.78 (t, J=6.5 Hz, 1H), 0.89 (t, J=5.0 Hz, 1H), 1.26 (s, 12H), 1.22-1.32 (m, 18H); $^{13}$C NMR (125.7 MHz, CDCl$_3$): δ 14.10, 22.61, 23.99, 24.61, 24.83, 31.68, 32.14, 32.81, 63.14, 82.91; $^{11}$B NMR (160.4 MHz, CDCl$_3$): δ +32.8 (s).

Cyclohexylboronic acid pinacolester (Table 1, entry 8); The spectroscopic data match those reported previously (*J. Org. Chem.* 1992, 12, 3482-3485). Colorless oil; 82% yield (0.856 g). $^1$H NMR (600 MHz, CDCl$_3$): δ 0.93-1.00 (m, 1H), 1.23 (s, 12H), 1.26-1.40 (m, 4H), 1.54-1.70 (m, 6H); $^{13}$C NMR (125.7 MHz, CDCl$_3$): δ 24.48, 26.56, 26.88, 27.72, 82.45; $^{11}$B NMR (160.4 MHz, CDCl$_3$): S+33.8 (s).

Tertiarybutylboronic acid pinacolester (Table 1, entry 9); The spectroscopic data match those reported previously (*J. Org. Chem.* 1986, 51, 337-342). Colorless oil; 65% yield (0.598 g). $^1$H NMR (500 MHz, CDCl$_3$): δ 0.94 (s, 9H), 1.23 (s, 12H); $^{13}$C NMR (125.7 MHz, CDCl$_3$): δ 24.61, 26.93, 82.87; $^{11}$B NMR (160.4 MHz, CDCl$_3$): δ +34.6 (s).

3-Pentylboronic acid pinacolester (Table 1, entry 10); Colorless oil; 98% yield (0.991 g). $^1$H NMR (500 MHz, CDCl$_3$): δ 0.89 (t, J=7.8 Hz, 6H), 0.94 (t, J=7.2, 1H), 1.24 (s, 12H), 1.41 (m, 4H); $^{13}$C NMR (125.7 MHz, CDCl$_3$): δ 13.48, 23.84, 24.65, 82.65; $^{11}$B NMR (160.4 MHz, CDCl$_3$): δ+34.2 (s).

Example 2

Synthesis and Reaction of Neopentylglycolborane with m-Tolylmagnesium Bromide

A solution of neopentylglycol (17.8 mmol, 1.85 g, 1.2 equiv) in dry THF (10 mL) was stirred and cooled to 0° C. A solution of BH$_3$.SMe$_2$ (15 mmol, 10 M in methyl sulfide) was added dropwise via syringe under argon. After 30 min of stirring at 0° C., the reaction mixture was warmed to 25° C.

and stirring was continued until no further evolution of hydrogen was observed (ca. 90 min). The solution was distilled under reduced pressure to isolate pure neopentylglycolborane as a clear oil. m-Tolylmagnesium bromide (10 mmol, 1 M) was added dropwise at 25° C. with constant stirring. The reaction was complete after 1 h as evidenced by the disappearance of neopentylglycolborane starting material (δ +26.9, d, J=176.0 Hz), and the appearance of a singlet at +28.0 ppm via $^{11}$B-NMR analysis. The reaction was then cooled to 0° C. (ice bath) and acidified with 3 M aqueous HCl (3 mL) (CAUTION: hydrogen evolution). After 10 min of stirring the reaction mixture was warmed to 25° C. and stirred for an additional 30 min. The reaction mixture was then transferred to a separatory funnel and extracted with diethyl ether (3×15 mL). The combined organic layers were dried over anhydrous MgSO$_4$, filtered, and dried under vacuo (25° C., 1 Torr) to afford m-tolyl pinacolborane as a pale yellow oil.

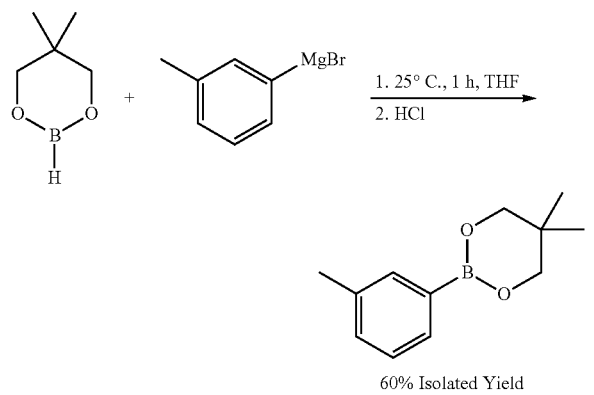

60% Isolated Yield

Colorless oil; 60% yield based on m-tolylmagnesium bromide (0.612 g). $^1$H NMR (500 MHz, CDCl$_3$): δ 1.03 (s, 6H), 2.37 (s, 3H), 3.78 (s, 4H), 7.277-7.289 (m, 2H), 7.616-7.630 (m, 1H), 7.649 (s, 1H). $^{13}$C NMR (125.7 MHz, CDCl$_3$): δ 21.92, 72.40, 127.70, 131.01, 131.60, 134.60, 137.31. $^{11}$B NMR (160.4 MHz, CDCl$_3$): δ +28.0 (s).

Example 3

Preparation of Aryl and Alkyl-Pinacolboranate Esters Under Barbier-Type Conditions The following procedure for the preparation m-tolyl pinacolborane is representative. A 25-mL round-bottom flask equipped with a magnetic stir bar was charged with magnesium turnings (0.058 g, 2.4 mmol) and was activated by addition of iodine crystals and warming until iodine sublimed. The flask was cooled to 25° C. and was purged with Ar. THF (3.5 mL) was added to the flask, followed by the addition of neat pinacolborane (0.29 mL, 2.0 mmol). m-Tolyl bromide (0.243 mL, 2.0 mmol) was then added drop wise over five minutes with constant stirring at 25° C. The reaction was complete after 3 h as evidenced by the disappearance of pinacolborane starting material (δ +27.7, d, J=173.9 Hz), and the appearance of a singlet at +30.6 ppm via $^{11}$B-NMR. The reaction was then cooled to 0° C. (ice bath) and acidified with 3 M aqueous HCl (3 mL) (CAUTION: hydrogen evolution). After 10 min of stirring the reaction mixture was warmed to 25° C. and stirred for an additional 30 min. Table entries 4, 6, 7, 8 were quenched with aqueous NH$_4$Cl (2.5 mL, 0.16 M). The reaction mixture was then transferred to a separatory funnel and extracted with diethyl ether (3×15 mL). The combined organic layers were dried over anhydrous MgSO$_4$, filtered, and dried under vacuo (25° C., 1 Torr) to afford m-tolyl pinacolborane as a pale yellow oil. The results for the other pinacolborane esters prepared by this method are summarized in Table 2.

TABLE 2

Synthesis of Boronate Esters Under Barbier Conditions[a]

| Entry | Product | Isolated Yield (%) |
|---|---|---|
| 1[a] | 4-Et-C$_6$H$_4$-Bpin | 99 |
| 2 | 3-Me-C$_6$H$_4$-Bpin | 99 |
| 3 | 1-pyrenyl-BPin | 78 |
| 4 | 2-PinB-biphenyl | 88 |
| 5 | 2-Me-4-MeO-C$_6$H$_3$-Bpin | 97 |
| 6 | 4-(CH(OMe)$_2$)-C$_6$H$_4$-Bpin | 87 |
| 7 | n-hexyl-Bpin | 86 |

TABLE 2-continued

Synthesis of Boronate Esters Under Barbier Conditions[a]

$$R_3\text{-Br} + Mg^o + HB\begin{pmatrix}O\\O\end{pmatrix}\xrightarrow{\text{THF, <3 h, 25° C.}} R_3\text{-B}\begin{pmatrix}O\\O\end{pmatrix}$$

| Entry | Product | Isolated Yield (%) |
|---|---|---|
| 8 | PinB-C6H4-Bpin (1,4) | 65[b] |
| 9 | PhCH(CH3)-BPin | 75[c] |
| 10 | 2-Thienyl-Bpin | 92 |
| 11 | 5-Cl-2-thienyl-Bpin | 75 |
| 12 | CH2=C(Ph)-Bpin | 80 |

[a]Reagents and conditions: Mg° (2.4 mmol), PinBH (2.0 mmol), anhydrous THF (4.0 mL), organohalide (2.0 mmol), argon, 25° C., 2-3 h.
[b]Required 2 eq of PinBH and 2 eq of Mg°.
[c]Required 2 eq of (1-bromoethyl)benzene.

4-Ethylphenylboronic acid pinacolester (Table 2, entry 1); The spectroscopic data match those reported previously (Organometallics 2008, 27, 6013-6019). Clear oil; 99% yield (0.483 g). $^1$H NMR (500 MHz, CDCl$_3$): δ 1.24 (t, J=6 Hz, 3H), 1.34 (s, 12H), 2.67 (q, J=7.5 Hz, 2H) 7.23 (d, J=8 Hz, 1H), 7.75 (d, J=8 Hz, 1H); $^{13}$C NMR (125.7 MHz, CDCl$_3$): δ 15.48, 24.87, 29.14, 83.71, 127.49, 135.05; $^{11}$B NMR (160.4 MHz, CDCl$_3$): S+30.8 (s).

m-Tolylboronic acid pinacolester (Table 2, entry 2); The spectroscopic data match those reported previously (J. Am. Chem. Soc. 2000, 122, 12868-12869). Clear oil; 99% yield (0.436 g). $^1$H NMR (500 MHz, CDCl$_3$): δ 1.36 (s, 12H), 2.379 (s, 3H), 7.26-7.29 (m, 2H), 7.63 (t, 1H), 7.65 (s, 1H), 7.54 (m, 1H); $^{13}$C NMR (125.7 MHz, CDCl$_3$): δ 21.31, 24.91, 83.70, 127.84, 131.93, 132.04, 132.20, 135.50, 137.28; $^{11}$B NMR (160.4 MHz, CDCl$_3$): δ +30.6 (s).

2-Pyreneboronic acid pinacolester (Table 2, entry 3); The spectroscopic data match those reported previously (Eur. J. Org. Chem. 2001, 3819-3829). Deep red oil; 78% yield (0.511 g). $^1$H NMR (500 MHz, CDCl$_3$): δ 1.51 (s, 12H), 8.125 (m, 7H), 8.57 (d, J=7.5 Hz, 1H), 9.11 (d, J=9.5 Hz, 1H); $^{13}$C NMR (125.7 MHz, CDCl$_3$): δ 25.12, 84.01, 124.22, 125.09, 125.33, 125.44, 125.85, 126.01, 127.53, 127.646, 127.94, 128.19, 128.68, 130.93, 131.30, 133.61, 134.023, 136.60; $^{11}$B NMR (160.4 MHz, CDCl$_3$): δ +22.50 (s), +31.9 (s).

2-Biphenylboronic acid pinacolester (Table 2, entry 4); The spectroscopic data match those reported previously (Synlett, 2006, 12, 1867-1870). Clear oil; 88% yield (0.351 g). $^1$H NMR (500 MHz, CDCl$_3$): δ 1.27 (s, 12H), 7.38-7.81 (m, 9H); $^{13}$C NMR (125.7 MHz, CDCl$_3$): δ 24.69, 83.87, 126.47, 127.03, 127.35, 127.45, 127.97, 128.50, 128.96, 129.17, 129.35, 130.01, 130.29, 134.67, 143.48, 147.75; $^{11}$B NMR (160.4 MHz, CDCl$_3$): δ +30.7 (s).

2-(4-Methoxy-2-methylphenyl)boronic acid pinacolester (Table 2, entry 5); Clear oil; 97% yield (0.483 g). $^1$H NMR (500 MHz, CDCl$_3$): δ 1.29 (s, 12H), 2.563 (s, 3H), 3.82 (s, 3H), 6.74 (m, 2H), 7.77 (d, J=7 Hz, 1H); $^{13}$C NMR (125.7 MHz, CDCl$_3$): δ 22.48, 24.94, 55.03, 83.22, 110.27, 115.65, 138.03, 147.40; $^{11}$B NMR (160.4 MHz, CDCl$_3$): δ +30.7 (s).

p-Benzaldehyde dimethyl acetal boronic acid pinacolester (Table 2, entry 6); Clear oil; 81% yield (0.450 g). $^1$H NMR (500 MHz, CDCl$_3$): δ 1.29 (s, 12H), 3.358 (s, 6H), 5.38 (s, 1H), 7.41 (d, J=7.5 Hz, 2H), 7.78 (d, J=8.5 Hz, 2H); $^{13}$C NMR (125.7 MHz, CDCl$_3$): δ 24.77, 24.88, 52.45, 52.65, 83.84, 102.89, 10.16, 126.16, 134.78, 141.05; $^{11}$B NMR (160.4 MHz, CDCl$_3$): δ +30.4 (s).

Octylboronic acid pinacol ester (Table 2, entry 7); The spectroscopic data match those reported previously (J. Am. Chem. Soc. 1996, 118, 909-910). Clear oil; 86% yield (0.411 g). $^1$H NMR (500 MHz, CDCl$_3$): δ 0.76 (t, J=7.5 Hz, 2H), 0.86 (t, J=7 Hz, 3H), 1.23 (s, 12H), 1.25 (s, 8H), 1.38 (m, 4H); $^{13}$C NMR (125.7 MHz, CDCl$_3$): δ 14.11, 22.70, 24.02, 24.81, 29.28, 29.40, 31.92, 32.46, 82.5; $^{11}$B NMR (160.4 MHz, CDCl$_3$): δ +33.7 (s).

1,4-Bisboronic acid pinacol ester benzene (Table 2, entry 8); The spectroscopic data match those reported previously (J. Am. Chem. Soc. 2000, 122, 8717-8727). Reaction stoichiometry: 1 eq 1,4-dibromobenzene, 2.2 eq of Mg° and 2.5 eq PinBH. Clear oil; 61% yield (0.404 g). $^1$H NMR (500 MHz, CDCl$_3$): δ 1.34 (s, 24H), 7.81 (s, 4H); $^{13}$C NMR (125.7 MHz, CDCl$_3$): δ 24.91, 134.02; $^{11}$B NMR (160.4 MHz, CDCl$_3$): δ +30.7 (s).

1-Boronic acid ethylbenzene pinacolester (Table 2, entry 9); Clear oil; 75% yield (0.351 g). $^1$H NMR (500 MHz, CDCl$_3$): δ 1.259 (s, 6H), 1.275 (s, 6H), 1.408 (d, 3H), 3.523 (q, 1H), 7.300 (m, 5H); $^{13}$C NMR (125.7 MHz, CDCl$_3$): δ 17.5, 24.8, 47.5, 48.8, 83.5, 125.1, 126.2, 127.9, 128.1, 144.9; $^{11}$B NMR (160.4 MHz, CDCl$_3$): δ +33.2 (s).

2-Thiopheneboronic acid pinacol ester (Table 2, entry 10); The spectroscopic data match those reported previously (J. Org. Chem. 2000, 65, 164-168). White solid; 92% yield (0.193.g). $^1$H NMR (500 MHz, CDCl$_3$): δ 1.36 (s, 12H), 7.21 (dd, J=3.5, 5 Hz, 1H), 7.65 (d, J=4.5 Hz, 1H), 7.67 (d, J=3.5 Hz, 1H); δ $^{13}$C NMR (125.7 MHz, CDCl$_3$): δ 24.75, 84.19, 128.36, 132.51, 137.32; $^{11}$B NMR (160.4 MHz, CDCl$_3$): δ +29.4 (s).

5-Chlorothiophene-2-boronic acid pinacol ester (Table 2, entry 11); The spectroscopic data match those reported previously (Bioorg. Med. Chem. 2005, 13, 2305-2312). Clear oil; 75% yield (0.360 g). IR (Nujol) 1019, 1056, 1146, 1211, 1302, 1377, 1463, 1522 cm$^{-1}$; $^1$H NMR (500 MHz, CDCl$_3$): δ 1.34 (s, 12H), 6.98 (d, J=3.5 Hz, 1H), 7.41 (d, J=4 Hz, 1H); $^{13}$C NMR (125.7 MHz, CDCl$_3$): δ 24.75, 84.38, 127.77, 136.91; $^{11}$B NMR (160.4 MHz, CDCl$_3$): δ +28.1 (s).

Alpha-vinylboronic acid pinacol ester (Table 2, entry 12); The spectroscopic data match those reported previously (J. Am. Chem. Soc. 2002, 124, 8001-8006). Clear oil; 75% yield (0.352 g). $^1$H NMR (500 MHz, CDCl$_3$): δ 1.35 (s, 12H), 6.0 (d, J=0.9 Hz, 1H), 6.11 (d, J=0.8 Hz, 1H), 7.27 (dt, J=1.5, 5.5

Hz, 1H), 7.34 (dt, J=2, 5.5 Hz, 1H), 7.516 (m, 1H); $^{13}$C NMR (125.7 MHz, CDCl$_3$): δ 24.86, 83.90, 127.16, 127.33, 128.33, 131.05, 141.56; $^{11}$B NMR (160.4 MHz, CDCl$_3$): δ +29.9 (s).

Example 4

Preparation of Allylpinacolboronate and Subsequent Reaction with Benzaldehyde

The following procedure for the preparation of allylpinacolboronate ester is representative. A 25-mL round-bottom flask equipped with a magnetic stir bar was charged with magnesium turnings (0.04 g, 1.65 mmol) and fitted with a rubber septum. The flask was purged with argon and charged with dry THF (2.3 mL) followed by PinBH (0.199 mL, 1.37 mmol). To the reaction mixture allylbromide (0.116 mL, 1.37 mmol) was added drop wise with constant stirring over five minutes at 25° C. After stirring for 30 min at 25° C., a second equivalent of allylbromide (0.116 mL, 1.37 mmol) was added. After 90 min of stirring at 25° C. the magnesium turnings were fully consumed and $^{11}$B NMR analysis confirmed the complete formation of allylpinacolboronate. Benzaldehyde (0.138 mL, 1.37 mmol) was then added and the reaction mixture was stirred for addition 12 h at 25° C. The reaction mixture was then diluted with hexane (5 mL), quenched with aqueous 1 M HCl (5 mL) and transferred to a separatory funnel. The organic layer was washed with aqueous 1 M NaOH (2×5 mL) and DI water (2×3 mL). The combined organic layers were dried over anhydrous MgSO$_4$, filtered, and dried under vacuo (25° C., 1 Torr) to afford 1-phenyl-3-buten-1-ol as a clear colorless oil; 94.5% (0.190 g). The results for the other allylpinacolborane esters prepared by this method are summarized in Table 3.

TABLE 3

Synthesis of Allylboronate Esters Under Barbier Conditions[a]

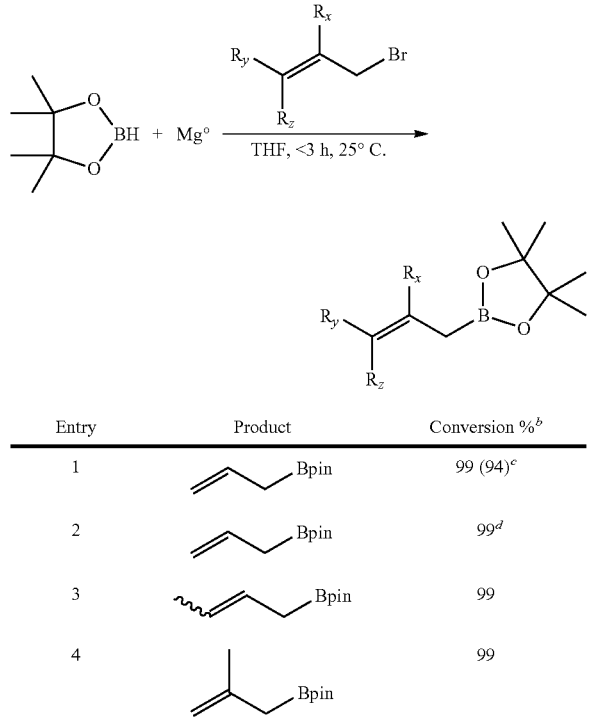

| Entry | Product | Conversion %[b] |
|---|---|---|
| 1 | ⟋⟋Bpin | 99 (94)[c] |
| 2 | ⟋⟋Bpin | 99[d] |
| 3 | ⟋⟋Bpin | 99 |
| 4 | (CH$_3$)$_2$C=CHCH$_2$Bpin | 99 |
| 5 | (CH$_3$)$_2$C=CHCH$_2$Bpin | 99 |
| 6 | CH$_2$=CHCH(CH$_3$)Bpin | 90[e,f] |
| 7 | CH$_2$=CHC(CH$_3$)$_2$Bpin | 95[e] |

[a]Reagents and conditions: Mg° (1.2 equiv), PinBH (1.0 equiv) in anhydrous THF to make 0.5-1.0M soln., allylhalide (2.0 equiv), argon, 25° C., 3 h.
[b]Conversion by $^{11}$B—NMR analysis.
[c]Isolated yield of allylboration product with benzaldehyde (see Experimental).
[d]Used allylchloride as starting halide.
[e]Yield of crude product.
[f]Isomeric mixture of crotyl bromide was used (E/Z ratio 90/10).

Allylboronic acid pinacol ester (Table 3, entry 1); $^{11}$B NMR (160.4 MHz, CDCl$_3$): δ +33.0 (s).

1-Phenyl-3-buten-1-ol (Table 3, entry 1); Clear/light yellow oil; 94% yield (0.190 g). $^1$H NMR (500 MHz, CDCl$_3$): δ 2.50-2.57 (m, 2H), 4.75 (dd, J=5, 7.5 Hz), 5.15-5.20 (m, 2H), 5.79-5.87 (m, 1H), 7.28-7.38 (m, 5H); $^{13}$C NMR (125.7 MHz, CDCl$_3$): δ 43.90, 73.39, 118.55, 125.97, 127.69, 128.56, 134.61, 144.04

Allylboronic acid pinacol ester (Table 3, entry 2); $^{11}$B NMR (160.4 MHz, CDCl$_3$): δ +33.2 (s).

Crotylpinacolboronate (Table 3, entry 3); $^{11}$B NMR (160.4 MHz, CDCl$_3$): δ +33.6 (s).

Methallylpinacolboronate (Table 3, entry 4); $^{11}$B NMR (160.4 MHz, CDCl$_3$): δ +33.1 (s).

Prenylpinacolboronate (Table 3, entry 5); $^{11}$B NMR (160.4 MHz, CDCl$_3$): δ +33.8 (s).

3-(4,4,5,5-Tetramethyl-1,3,2-dioxaborolane-2-yl)-but-1-ene (Table 3, Entry 6); The spectroscopic data match those reported previously (J. Organomet. 1980, 195, 137-146; J. Chem. Ber. 1991, 124, 563-569). An isomeric mixture of crotyl bromide was used (E/Z ration 90/10). Clear oil; 90% yield (0.224 g). $^1$H NMR (500 MHz, CDCl$_3$): δ 1.09 (d, J=7.5 Hz, 3H), 1.23 (s, 12H), 1.89 (quint, J=7.5 Hz, 1H), 4.92 (app dt, J=10 Hz, 2H), 4.97 (app dt, J=17.5 Hz, 2H), 5.90-5.97 (m, 1H). $^{13}$C NMR (125.7 MHz, CDCl$_3$): δ 14.1, 24.6, 25.5, 83.2, 112.0, 141.0. $^{11}$B NMR (160.4 MHz, CDCl$_3$): δ +33.1 (s).

3-(3,3,5,5-Tetramethyl-1,3,2-dioxaborolane-2-yl)-3-methylbut-1-ene (Table 3, Entry 7); The spectroscopic data match those previously reported (*J. Organomet.* 1980, 195, 137-146). The starting halide was 1-bromo-3-methylbut-2-ene. Clear oil; 95% yield (0.242 g). $^1$H NMR (500 MHz, CDCl$_3$): δ 1.07 (s, 6H), 1.22 (s, 12H), 4.90 (dd, J=0.5, 0.5 Hz, 1H), 4.93 (dd, J=0.3, 0.6 Hz, 1H), 5.96 (dd, J=5.7, 3.3 Hz, 1H). $^{13}$C NMR (125.7 MHz, CDCl$_3$): δ 23.4, 24.5, 83.2, 110.0, 146.7. $^{11}$B NMR (160.4 MHz, CDCl$_3$): δ +33.9 (s).

Example 5

$^{11}$B NMR Studies of Reaction of p-Tolylmagnesium Bromide with Pinacolborane

Freshly prepared p-tolylmagnesium bromide was reacted with a PinBH/THF solution at 25° C. After 1 h of stirring at 25° C. an aliquot of the reaction mixture was analyzed by $^{11}$B-NMR spectroscopy. The $^{11}$B-NMR spectrum showed essentially quantitative formation of the p-tolylpinacolboronate ester. Under these conditions the initially formed dialkoxyarylborohydride adduct ("ate" complex) was not observed, but without being bound by any theory, if such an intermediate formed it may have rapidly disproportionated to the product pinacolboronate ester and HMgBr as shown in Scheme 1.

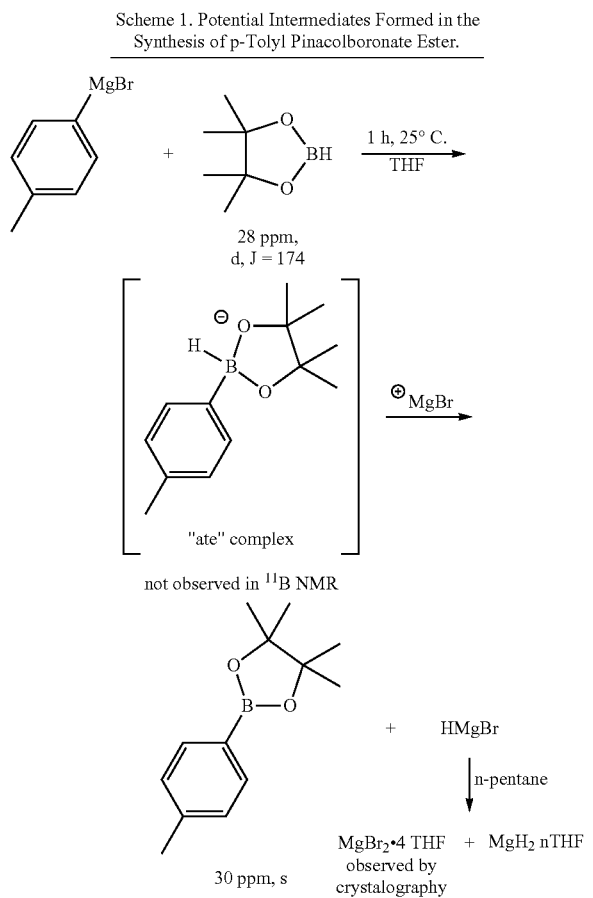

Scheme 1. Potential Intermediates Formed in the Synthesis of p-Tolyl Pinacolboronate Ester.

Typically, dialkoxymonoalkylborohydride species display a broad singlet in the region of 0 to +10 ppm in the $^{11}$B NMR spectrum. They are also known to transfer their elements of metal hydride to more Lewis acidic di- and trialkylborates. The above reaction was carried out under non-stirring conditions, and showed that multiple additions occurred to afford products, such as dialkylborohydride (t, −10 ppm), trialkylborohydride (d, −14 ppm), and tetraalkylborate (s, −16 ppm). Without being bound by any theory, localized hot spots may cause disproportionation of PinBH and eventually multiple addition of Grignard reagent. The dialkyl- and trialkylborane formed under non-stirring conditions may react with initially formed dialkoxyorganoborohydrides to give the corresponding borohydrides. Consequently, it is important to carry out the reaction of Grignard reagents with PinBH at ambient temperature (0-25° C.) with constant stirring.

During our investigation on boronate ester synthesis from Grignard reagents, Dunach et al. reported a synthesis of benzyl boronate esters by catalytic reductive coupling between benzyl bromides and PinBH. *J. Am. Chem. Soc.* 2010, 132, 11825-11827. They reported using 10 mol % of magnesium metal)(Mg$^0$ and stoichiometric amounts of triethylamine (Et$_3$N) under refluxing conditions in THF for 15 h. They also claimed that they observed the initial adduct, dialkoxymonalkylborohydride, at δ −9.7 ppm (d, J=86 Hz). However, this chemical shift is more likely attributable to a trialkylborohydride species that generally have a chemical shift range of δ −10 to −17 ppm. Based on the above spectroscopic observations, the $^{11}$B NMR data reported by Dunach et al. may correspond to tribenzylborohydride rather than to benzylpinacolborohydride.

Example 6

Characterization of MgH$_2$ and MgBr$_2$ Byproducts of the Reaction of p-Tolylmagnesium Bromide with Pinacolborane Without being bound by any theory, the reaction may proceed through a pathway where hydridomagnesium bromide (HMgBr) acts as the leaving group. By a slow pentane vapor diffusion technique, crystals suitable for x-ray analysis were obtained from the reaction mixture of p-tolylmagnesium bromide and pinacolborane. The x-ray diffraction results showed that the crystal was MgBr$_2$(THF)$_4$, a known compound. Ashby et al. have reported isolating MgBr$_2$(THF)$_4$ while attempting to crystallize HMgBr. *J. Am. Chem. Soc.* 1977, 99, 310-311. Without being bound by any theory, if formed, HMgBr may undergo disproportionation to MgH$_2$ and MgBr$_2$. The absence of any hydride containing species in the isolated crystals suggested that the MgH$_2$ species was soluble in THF/pentane mixture and did not precipitate upon pentane addition. Aliquots of the reaction solution were quenched with water/methanol and the number of moles of H$_2$ gas evolved was measured. The experimentally measured molarity of MgH$_2$ (magnesium hydride) in THF/pentane was in 98% agreement with the theoretical value. In addition, the MgH$_2$ byproduct was qualitatively identified by trapping it with addition of one equivalent BH$_3$:THF at 25° C. for 2 h. The $^{11}$B-NMR analysis of an aliquot showed the formation of a borohydride as a quintet at −40 ppm and the complete absence of the signal due to BH$_3$:THF at 0 ppm.

Example 7

Density Functional Theory (DFT) Calculations on the Disproportionation of 2 equiv. of HMgBr to MgBr$_2$ and MgH$_2$ The disproportionation of 2 HMgBr to MgBr$_2$ and MgH$_2$ was calculated using DFT (Gaussian09) at the B3LYP/6-31G (d) level of theory with the PCM polarized continuum solvent model (solvent=THF) for geometry optimization and final energy. The DFT results show that the calculated reaction is endothermic by 2.3 kcal/mol. Also, the DFT results indicate that formation of the bridged complex HMg(μ-H,Br)MgH from 2 HMgBr (FIG. 1) is exothermic by −21.0 kcal/mol. The calculated μ(H,H) bridged dimer is more stable at −21.4 kcal/mol and the calculated μ(Br,Br) bridged dimer is less stable at −18.9 kcal/mol, but the μ(H,Br) bridged dimer may enable the disproportionation by breaking opposite bonds of the bridge. As a model for THF, dimethyl ether (DME) was chosen for explicit coordination together with PCM (solvent=THF). The reaction in Scheme 1 was shown experimentally to occur in pure diethyl ether, making dimethyl ether a good computational model. The calculated disproportionation of two octahedral HMgBr-DME$_4$ to octahedral MgBr$_2$-DME$_4$+MgH$_2$-DME$_4$ was found to be slightly exothermic by −0.51 kcal/mol. The calculated formation of the bisoctahedral DME$_3$HMg(μ, H,Br)MgBrDME$_3$ intermediate from HMgBr-DME$_4$ is endothermic by +0.45 kcal/mol, thus explicit solvation favors product formation. Without being bound by any theory, the DFT calculations provide support for a disproportionation reaction producing the observed byproducts in the reaction.

Example 8

Preparation of Aryl Boronic Acids From Dialkylaminoborane

The following procedure for the preparation of o-tolyl boronic acid is representative. Diisopropylaminoborane was synthesized by reacting the corresponding LAB reagent with trimethylsilyl chloride (TMSCl) at 25° C. The LAB reagent is obtained by reaction of borane/dimethylsulfide complex (BMS or BH$_3$:DMS) and diisopropylamine followed by dehydrogenation with n-butyl lithium (Scheme 2).

Scheme 2. Synthesis of Lithium
Diisopropylaminoborohydride and Diisopropylaminoborane

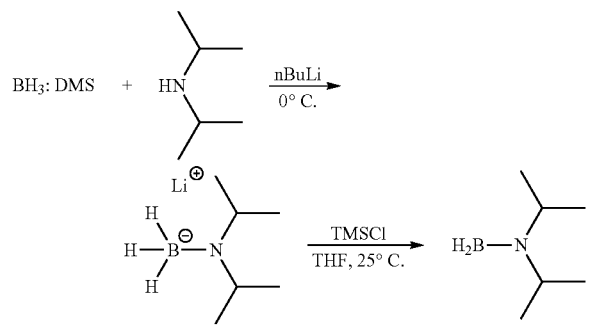

A 50-mL round-bottom flask equipped with a magnetic stir bar and fitted with rubber septum was charged with diisopropylaminoborane (2.4 mL, 2.4 mmol, 1.2 eq.). o-tolyl magnesium bromide (2 mL, 2.0 mmol, 1 eq.) was added dropwise over 5 min via syringe while stirring at 0° C. (ice bath). After 1 hr, with the reaction still on ice, 3 M HCl (5 mL) was added dropwise over 5 min. and allowed to stir for 30 min. The reaction mixture was then refluxed for 15 min. Following reflux, the solution was transferred to a separatory funnel and extracted with Et$_2$O (2×15 mL). The organic layers were combined and extracted with 1 M HCl (4×15 mL), dried with anhydrous MgSO$_4$, and evaporated in vacuo (25° C., 1 Torr) to afford o-tolylphenyl boronic acid as a white powder (Table 4, Entry 2). For other boronic acids prepared by this method see Table 4, Entries 1 and 3-11. Phenylmagnesium bromide smoothly converted to boronic acid in a reaction time of less than 30 minutes at −45° C. (Table 4, Entry 7). When this same reaction was carried out at −78° C. the reaction mixture would freeze, requiring flask removal from cryogenic conditions. The mixture was allowed to warm until the magnet bar was free flowing, in which case the reaction was returned to cryogenic conditions. Though the reaction was not maintained at a constant temperature, the isolated boronic acid yield was 95% (Table 4, Entry 8).

Evaporation of residual solvent provided the analytically pure product as white solid. Because of their facile dehydration, boronic acids tend to provide inconsistent melting points. Therefore, the melting points for boronic acids were not taken.

phenylboronic acid (Table 4, Entries 1, 7, and 8); White powder; 95% yield (0.234 g). $^1$H NMR (500 MHz, CDCl$_3$): δ 7.52 (t, J=6 Hz, 1H), 7.608 (t, J=7 Hz, 1H), 8.26 (d, J=5.5 Hz, 1H); $^{13}$C NMR (125.7 MHz, CDCl$_3$): δ 128.03, 132.74, 135.69; $^{11}$B NMR (160.4 MHz, CDCl$_3$): δ +28.61.

o-tolylboronic acid (Table 4, Entry 2); White powder; 88% yield (0.226 g). $^1$H NMR (500 MHz, CDCl$_3$): δ 2.820, 7.276 (m, 2H), 7.459 (dt, J=1.5, 7 Hz, 1H), 8.223 (dd, J=7 Hz, 1H); $^{13}$C NMR (125.7 MHz, CDCl$_3$): δ 23.11, 125.31, 130.73, 132.34, 137.37, 146.42; $^{11}$B NMR (160.4 MHz, CDCl$_3$): δ +31.9.

m-tolylboronic acid (Table 4, Entry 3); White powder; 88% yield (0.458 g). $^1$H NMR (500 MHz, CDCl$_3$): δ 2.82, 7.28 (m, 2H), 7.46 (dt, J=1.5, 7 Hz, 1H), 8.22 (dd, J=7 Hz, 1H); $^{13}$C NMR (125.7 MHz, CDCl$_3$): δ 23.1, 125.3, 130.7, 132.3, 137.4, 146.4; $^{11}$B NMR (160.4 MHz, CDCl$_3$): δ +31.9.

p-tolylboronic acid (Table 4, Entry 4); White powder; 95% yield (0.345 g). $^1$H NMR (500 MHz, CDCl$_3$): δ 2.44 (s, 3H), 7.32 (d, J=7.5 Hz, 1H), 8.13 (d, J=7.5 Hz, 1H); $^{13}$C NMR (125.7 MHz, CDCl$_3$): δ 21.9, 128.9, 133.7, 135.9, 143.1; $^{11}$B NMR (160.4 MHz, CDCl$_3$): δ +30.43.

2-methoxyphenylboronic acid (Table 4, Entry 5); White powder; 95% yield (0.420 g). $^1$H NMR (500 MHz, CDCl$_3$): δ 2.44 (s, 3H), 7.32 (d, J=7.5 Hz, 1H), 8.13 (d, J=7.5 Hz, 1H); $^{13}$C NMR (125.7 MHz, CDCl$_3$): δ 21.9, 128.9, 133.7, 135.9, 143.1; $^{11}$B NMR (160.4 MHz, CDCl$_3$): δ +28.61.

t-butylboronic acid (Table 4, Entry 6); White powder; 94% yield (0.481 g). $^{13}$C NMR (125.7 MHz, CDCl$_3$): δ 27.8; $^{11}$B NMR (160.4 MHz, CDCl$_3$): δ +32.7.

cyclohexylboronic acid (Table 4, Entry 9); White powder; 97% yield (0.497 g). $^{13}$C NMR (125.7 MHz, CDCl$_3$): δ 27.3, 27.5, 28.3; $^{11}$B NMR (160.4 MHz, CDCl$_3$): δ +33.5.

n-hexylboronic acid (Table 4, Entry 10); White powder; 78% yield (0.404 g). $^{13}$C NMR (125.7 MHz, CDCl$_3$): δ 14.7, 23.4, 24.2, 25.0, 32.5, 32.8; $^{11}$B NMR (160.4 MHz, CDCl$_3$): δ +34.4.

n-decylboronic acid (Table 4, Entry 11); White powder; 95% yield (0.888 g). $^{13}$C NMR (125.7 MHz, CDCl$_3$): δ 14.1, 22.7, 23.4, 24.4, 29.4, 29.5, 29.7, 31.9, 32.4; $^{11}$B NMR (160.4 MHz, CDCl$_3$): δ +33.9

Example 9

General Procedure for the Preparation of Aryl Boronic Acids Under Barbier Conditions The following procedure for the preparation of 1-napthyl-boronic acid is representative. A 25-mL round-bottom flask equipped with a condenser and magnetic stir bar was charged with magnesium turnings (0.058 g, 2.4 mmol) and was activated by addition of iodine crystals and warming until iodine sublimed. The flask was cooled to 25° C. and was purged with Ar. BH$_2$—N(iPr)$_2$ (2.4 mL, 2.4 mmol) was added to the flask and brought to reflux.

1-bromonapthylene (1.5 M, 2.0 mmol) was then added dropwise over five minutes with constant stirring at 65° C. The reaction was complete after 4 h as evidenced by the disappearance of BH$_2$—N(iPr)$_2$ starting material (δ 35, t, J=125 Hz), and the appearance of a doublet at (δ 38, d, J=112 Hz) with the corresponding magnesium aminoborohydride signal (MgBr$^+$ -BH$_3$—NiPr$_2$, δ −28, q, J=88 Hz). The reaction was then cooled to 25° C. and acidified with 3 M aqueous HCl (3 mL) (CAUTION: hydrogen evolution). After 10 min of stirring the reaction mixture was warmed to 65° C. and stirred for an additional 15 min. The reaction mixture was then transferred to a separatory funnel and extracted with diethyl ether (3×15 mL). The combined organic layers were dried over anhydrous MgSO$_4$, filtered, and dried under vacuo (25° C., 1 Torr) to afford 1-napthylboronic acid as a white solid (Table 4, Entry 10). The results for the other boronic acids prepared by this method are summarized in Table 4, Entries 12-16.

1-napthylboronic acid (Table 4, entry 12): White powder; 79% yield (0.253 g). $^1$H NMR (500 MHz, DMSO-d$_6$): δ 3.44 (brs, 1H), 7.50 (m, 3H), 7.78 (d, J=5 Hz, 1H), 7.91 (t, J=9.5 Hz, 2H), 8.36 (brs, OH), 8.42 (dd, J=8 Hz, 1 Hz, 1H); $^{13}$C NMR (125.7 MHz, DMSO-d$_6$): δ 128.2, 128.8, 129.1, 132.0, 132.9, 135.7; $^{11}$B NMR (160.4 MHz, DMSO-d$_6$): δ +30.2

4-methoxyboronic acid (Table 4, entry 13): White powder; 67% yield (0.196 g). $^1$H NMR (500 MHz, CDCl$_3$): δ 3.89 (s, 3H), 7.03 (d, J=8.5 Hz, 2H), 8.17 (d, J=8.5 Hz, 2H); $^{13}$C NMR (125.7 MHz, CDCl$_3$): δ 55.3, 113.7, 137.7, 163.4; $^{11}$B NMR (160.4 MHz, CDCl$_3$): δ +29.1.

2-Thiopheneboronic acid (Table 4, entry 14): White powder; 67% yield (0.221 g). $^1$H NMR (500 MHz, CDCl$_3$): δ 7.33 (dd, J=3.5, 4.5 Hz, 1H), 7.83 (d, J=4.5 Hz, 1H), 8.06 (d, J=4 Hz, 1H); $^{13}$C NMR (125.7 MHz, CDCl$_3$): δ 128.9, 135.1, 139.8; $^{11}$B NMR (160.4 MHz, CDCl$_3$): δ +27.0.

Allylboronic acid (Table 1, entry 15): $^{11}$B NMR (160.4 MHz, CDCl$_3$): d+42.1 (d, J=147 Hz), +36.6 (t, J=129 Hz).

1-Boronic acid ethylbenzene (Table 1, entry 16): $^{11}$B NMR (160.4 MHz, CDCl$_3$): d+42.1 (d, J=147 Hz, 1H), +36.6 (t, J=123 Hz, 2H).

TABLE 4

Boronic Acid Synthesis Substrate Profile Using Preformed Grignard Reagents[a] and Under Barbier Conditions[c]

H$_2$B—N(iPr)$_2$ (1.2 eq) + R$_4$—MgBr → (0° C., THF, 1 h) → H$_3$O$^+$ → R$_4$—B(OH)$_2$

| Entry | Substrate | Yield[b] % |
|---|---|---|
| 1 | phenyl-B(OH)$_2$ | 95 |
| 2 | 2-methylphenyl-B(OH)$_2$ | 88 |
| 3 | 3-methylphenyl-B(OH)$_2$ | 88 |
| 4 | 4-methylphenyl-B(OH)$_2$ | 95 |
| 5 | 2-methoxyphenyl-B(OH)$_2$ | 95 |
| 6 | tert-butyl-B(OH)$_2$ | 94 |
| 7 | phenyl-B(OH)$_2$ | 90[d,e] |
| 8 | phenyl-B(OH)$_2$ | 95[f,e] |
| 9 | cyclohexyl-B(OH)$_2$ | 97 |

TABLE 4-continued

Boronic Acid Synthesis Substrate Profile Using Preformed Grignard Reagents[a] and Under Barbier Conditions[c]

$$H_2B-N(iPr)_2 + R_4-MgBr \xrightarrow[THF, 1h]{0°C.} \xrightarrow{H_3O^+} R_4-B(OH)_2$$

1.2 eq

| Entry | Substrate | Yield[b] % |
|---|---|---|
| 10 | CH$_3$(CH$_2$)$_5$–B(OH)$_2$ | 78 |
| 11 | nC$_{10}$H$_{21}$–B(OH)$_2$ | 95 |
| 12 | 1-naphthyl–B(OH)$_2$ | 79[c] |
| 13 | MeO-C$_6$H$_4$–B(OH)$_2$ | 67[c] |
| 14 | 2-thienyl–B(OH)$_2$ | 84[c] |
| 15 | allyl–B(OH)$_2$ | <50[c,g] |
| 16 | CH$_3$CH(Ph)–B(OH)$_2$ | <50[c,g] |

[a]Reagents and conditions: BH$_2$—N(iPr)$_2$ (1M, 2.4 mmol), Grignard reagent (1M, 2.0 mmol), argon, 0° C., 1 h.
[b]Isolated yields of boronic acid are reported after aqueous workup.
[c]Reagents and conditions: Mg$^0$ (2.4 mmol), BH$_2$—N(iPr)$_2$ (1M, 2.4 mmol), anhydrous THF (4.0 mL), organohalide (2.0 mmol), argon, 65° C., 2-3 h.
[d]Reaction temperature of −45° C.
[e]Crude yield.
[f]Reaction temperature of −78° C.
[g]Conversion based on $^{11}$B NMR.

Example 10

$^{11}$B NMR Studies of Reaction of p-Tolylmagnesium Bromide with Diisopropylaminoborane p-Tolylmagnesium bromide 2 was reacted with 1 equiv. of BH$_2$—N(iPr)$_2$ 1 at 0° C. in THF as shown in Scheme 3.

Scheme 3. Addition Products Observed by $^{11}$B NMR Spectroscopy.

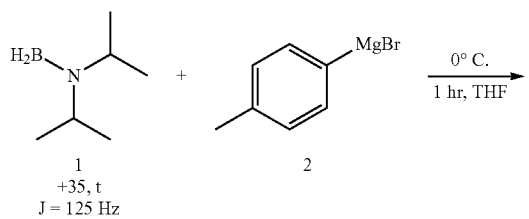

1
+35, t
J = 125 Hz

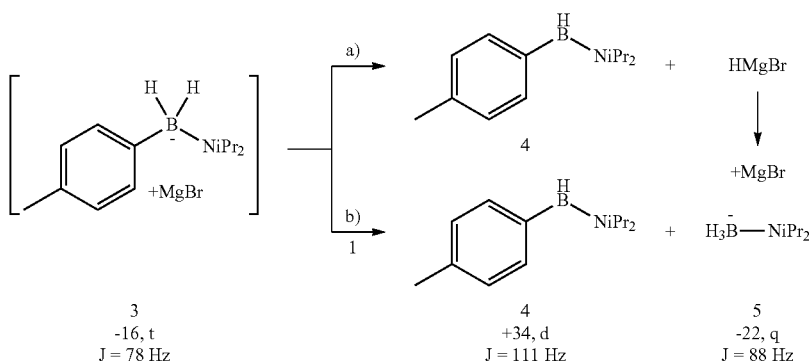

3
−16, t
J = 78 Hz

4
+34, d
J = 111 Hz

5
−22, q
J = 88 Hz $^{11}$B-NMR analysis at 30 minutes revealed the absence of 1 (δ 35, t, J=125 Hz) and the appearance of the single addition (B—H) aryl aminoborane adduct (δ 38, d, J=111 Hz) 4 and the known compound bromomagnesium aminoborohydride (MgBr$^+$ $^-$BH$_3$—NiPr$_2$, δ −22, q, J=88 Hz) 5. The $^{11}$B-NMR spectrum also showed small amounts of the initially formed bromomagnesium aryl(diisopropylamino)borohydride adduct (δ −12, t, J=78 Hz) 3. Under the reaction conditions, 3 is a fleeting intermediate, losing the majority of its hydride by two possible routes.

Without being bound by any theory, the observed products 4 and 5 could be formed in one of two routes or possibly both routes, although other alternatives are possible. In route A, the initially formed BH$_2$-arylaminoborohydride may disproportionate to form the single addition aryl aminoborane adduct (δ 38, d, J=112 Hz) and hydridomagnesium chloride (HMgCl). Conversely, in route B, the BH$_2$-arylaminoborohydride adduct may transfer a hydride to BH$_2$—N(iPr)$_2$. It was found that only 0.2 equivalents excess of BH$_2$—N(iPr)$_2$ was required for greater than 90% conversion to the boronic acid. This result indicated that the reaction pathway did not solely proceed through route B, as two equivalents of BH$_2$—N(iPr)$_2$ would be required for quantitative conversion to the boronic acid.

Without being bound by any theory, some amount of BH$_2$—N(iPr)$_2$, approximately 0.2 equivalents, is converted to the Mg$^+$ $^-$BH$_3$—NiPr$_2$. In route A, HMgCl would need to be a strong enough reductant to transfer a hydride to BH$_2$—N(iPr)$_2$. HMgCl is a known compound which does not undergo reductive elimination, but is a mild reducing agent soluble in THF. In a previous study, THF solvated HMgCl was quantitatively produced through the reaction of isopropylmagnesium chloride and pinacolborane in THF (Scheme 4). To the reaction mixture of iPrBPin and HMgCl was added 1 equivalent of BH$_2$—N(iPr)$_2$. Through $^{11}$BNMR analysis of the reaction mixture it was clear that there was no hydride transfer from HMgCl to BH$_2$—N(iPr)$_2$. Quantifying the distribution between route A and B could be carried out by measuring the amount of HMgCl present in the product mixture by hydrogen gas analysis.

Scheme 4. Investigation of the Ability of Hydridomagnesium Chloride to Transfer Hydride to BH$_2$NiPr$_2$.

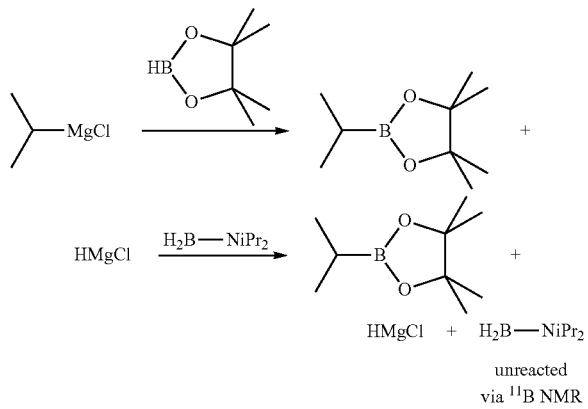

After the reaction depicted in Scheme 3 had completed, the aryl aminoborane adduct was converted to the corresponding boronic acid through an acidic quench on ice followed by a 15 minute reflux. The solution was analyzed by $^{11}$B-NMR following the quench showing the disappearance of the aryl aminoborane adduct and aminoborohydride peaks and the appearance of a singlet (δ 24) corresponding to the boronic acid and quartet (δ −26) attributable to an amineborane complex by its J value of 98 (Scheme 5). The boronic acid was then separated from the amineborane by liquid-liquid extraction.

Scheme 5. Acid quench of reaction mixture.

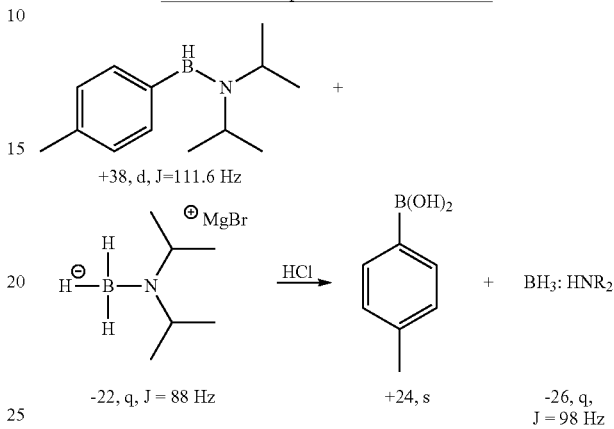

REFERENCES

Miyaura et al., Synth Commun. 1981, 11, 513; Miyaura and Suzuki, Chem. Rev. 1995, 95, 2457; Cepanec, Synthesis Of Biaryls, Oxford Uk: Elsevier Ltd., 2004; Ley and Thomas, Angew. Chem. Int. Ed. 2003, 42, 5400; Takaya et al., J. Am. Chem. Soc. 1998, 120, 5579; Takaya et al., Tet. Asymm. 1999, 10, 4047; Hayashi et al., J. Am. Chem. Soc. 2001, 123, 9918; Wu et al., Org. Lett. 2004, 6, 2701; Duan et al., Angew. Chem. Int. Ed. 2008, 47, 4351; Schneider et al., J. Am. Chem. Soc. 2008, 130, 13824; Wada et al., J. Am. Chem. Soc. 2004, 126, 8910; Trincado and Ellman, Angew. Chem. Int. Ed. 2008, 47, 5623; Lou et al., J. Am. Chem. Soc. 2007, 129, 15398; Hall, Synlett, 2007, 11, 1644; Sugiura et al., J. Am. Chem. Soc. 2004, 126, 7182; Kobayashi et al., Chem. Commun. 2005, 104; Sugiura et al., J. Am. Chem. Soc. 2006, 128, 11038; Brown and Cole, Organomet. 1983, 2, 1316; Murphy et al., Org. Lett. 2007, 9, 757; Ishiyama And Miyaura, Chem. Rec. 2004, 3, 271-280; Ishiyama et al., Org. Chem. 1995, 60, 7508-7510; Murata et al., J. Org. Chem. 1997, 62, 6458-6459; Murata et al., J. Org. Chem. 2000, 65, 164-168; Leowanawat et al., J. Org. Chem. 2010, 75, 7822-7828; Rosen et al., Org. Lett. 2008, 10, 2597-2600; Ishiyama and Miyaura, Organomet. Chem. 2003, 680, 3-11; Kikuchi et al., Tetrahedron, 2008, 64, 4967-4971; Cho et al., J. Am. Chem. Soc. 2000, 122, 12868-12869; Khotinsky and Melamed, Ber. 1909, 54, 2784; Gilman and Vernon, J. Am. Chem. Soc. 1926, 48, 1063-1066; Beinhoff et al., Eur. J. Org. Chem. 2001, 3819-3829; Tucker et al., J. Org. Chem. 1992, 57, 3482-3485; Kikuchi et al., Tetrahedron 2008, 64, 4967-4971; Molander and Ellis, J. Org. Chem. 2008, 73, 6841; Suginome et al., Organometallics 2000, 19, 4647-4649; Clegg et al., J. Acta Cryst. 1996, 52, 2545-2547; Lesley et al., Organometallics 1996, 15, 5137-5154; Brown et al., J. Org. Chem. 1986, 51, 337-342; Brown and Hubbard, J. Am. Chem. Soc. 1979, 101, 3964-3965; Pntaric et al., J. Am. Chem. Soc. 2010, 132, 11825-11827; Schroder and Spandau, Naturwissenschaften, 1966, 53, 360; Ashby and Goel, J. Am. Chem. Soc. 1977, 99, 310-311; Brown et al., "Organic Synthesis Via Boranes";

Wiley-Interscience: New York, 1975; Tucker et al., J. Org. Chem. 1992, 57, 3482-3485; Rosen et al., Org. Lett. 2008, 10, 2597-2600; Ishiyama et al., Tetradedron Lett. 1997, 38, 3447; Fisher et al., Tetrahedron Lett. 2002, 33, 4533; Pasumansky et al., J. Org. Chem. 2008, 73, 1898-1905; Singaram et al., Organometallics 1984, 3, 774; Pasumansky et al., J. Org. Chem. 2008, 73, 1898-1905; Tagaki et al. J. Am. Chem. Soc. 2002, 124, 8001-8006; Hartwig et al. J. Am. Chem. Soc. 2005, 127, 14263-14278; Hartwig et al. Organometallics 2008, 27, 6013-6019; Murata et al. Synlett, 2006, 12, 1867-1870; Pereira et al. J. Am. Chem. Soc. 1996, 118, 909-910; Iovine et al. J. Am. Chem. Soc. 2000, 122, 8717-8727; Ebdrup Bioorg. Med. Chem. 2005, 13, 2305-2312; Dunach et al. WO 2010/055245; Ishiyama et al. J. Am. Chem. Soc. 2002, 124, 390-391 Hoffman et al. J. Organomet. 1980, 195, 137-146; Hoffman et al. J. Chem. Ber. 1991, 124, 563-569; Roush et al. J Am. Chem. Soc. 1986, 108, 3422; and Chen et al. J. Org. Chem. 1999, 64, 9704.

What is claimed is:

1. A process for preparing a boronic ester compound of formula (I):

wherein $BH(OR_1)(OR_2)$ is selected from the group consisting of pinacolborane, catecholborane, neopentylglycolborane, and mixtures thereof; $R_3$ is selected from the group consisting of optionally substituted C1-C10 alkyl, optionally substituted C2-C10 alkenyl, and optionally substituted C3-C6 allyl; the alkyl, alkenyl, and allyl may contain one heteroatom selected from the group consisting of nitrogen, oxygen and sulfur in place of one carbon atom, and may be optionally substituted with one or more substituents independently selected from the group consisting of C1-C8 alkyl substituents and C2-C8 alkenyl substituents;

the process comprising combining a Grignard reagent with $BH(OR_1)(OR_2)$ in an ethereal solvent to form a reaction mixture; and maintaining the reaction mixture at a reaction temperature of from 0° C. to 50° C. to produce the boronic ester compound of formula (I) at a yield of at least 65%.

2. The process of claim 1, wherein the $BH(OR_1)(OR_2)$ is selected from the group consisting of pinacolborane, neopentylglycolborane, and mixtures thereof.

3. The process of claim 1, wherein the Grignard reagent is generated from an $R_3$-halide compound and $Mg^0$.

4. The process of claim 3, wherein about 1.2 equivalents of $Mg^0$, about 1.0 equivalents of $R_3$-halide, and about 1.0 equivalents of $BH(OR_1)(OR_2)$ are combined to form the reaction mixture.

5. The process of claim 1, wherein the process is carried out in the absence of a base.

6. The process of claim 1, wherein the ethereal solvent is selected from the group consisting of dimethyl ether, diethyl ether, dimethoxyethane, tetrahydrofuran, tetrahydropyran, dioxane, and anisole.

7. The process of claim 1, wherein the process further comprises hydrolyzing the boronic ester compound to form a boronic acid compound.

8. A process for preparing a boronic acid compound of formula (II):

wherein $R_4$ is selected from the group consisting of optionally substituted C1-C10 alkyl, optionally substituted C2-C10 alkenyl, optionally substituted C2-C10 allyl, optionally substituted C5-C12 aryl, and optionally substituted C7-C12 arylalkyl; the alkyl, alkenyl, allyl, aryl, and arylalkyl may contain one heteroatom selected from the group consisting of nitrogen, oxygen and sulfur in place of one carbon atom, and may be optionally substituted with one or more substituents independently selected from the group consisting of C1-C8 alkyl substituents, C2-C8 alkenyl substituents, C6-C10 aryl substituents and $OR_5$ substituents, wherein $R_5$ is C1-C8 alkyl, the process comprising combining a Grignard reagent with an optionally substituted dialkylaminoborane in an ethereal solvent to form a reaction mixture; and maintaining the reaction mixture at a reaction temperature of from −78° C. to 25° C. to produce the boronic acid compound of formula (II).

9. The process of claim 8, wherein the optionally substituted dialkylaminoborane is diisopropylaminoborane.

10. The process of claim 8, wherein the ethereal solvent is selected from the group consisting of dimethyl ether, diethyl ether, dimethoxyethane, tetrahydrofuran, tetrahydropyran, dioxane, and anisole.

11. The process of claim 1, wherein the ethereal solvent is tetrahydrofuran.

12. The process of claim 8, wherein the ethereal solvent is tetrahydrofuran.

13. The process of claim 1, wherein $R_3$ is a C1-C10 alkyl.

14. The process of claim 1, wherein $R_3$ is a C4-C8 cycloalkyl.

15. The process of claim 1, wherein $R_3$ is selected from the group consisting of methyl, ethyl, n-propyl, isopropyl, n-butyl, iso-butyl, sec-butyl, tert-butyl, n-pentyl, n-hexyl, n-heptyl, n-octyl, n-nonyl, n-decyl, cyclopentyl, cyclohexyl, cycloheptyl, and cyclooctyl.

16. The process of claim 1, wherein $R_3$ is a C2-C10 alkenyl.

17. The process of claim 1, wherein $R_3$ is a C4-C8 cycloalkenyl.

18. The process of claim 1, wherein $R_3$ is selected from the group consisting of vinyl, α-vinylbenzene, pentenyl, hexenyl, heptenyl, octenyl, nonenyl, decenyl, cyclohexenyl, cycloheptenyl, and cyclooctenyl.

19. The process of claim 1, wherein $R_3$ is a C3-C6 allyl.

20. The process of claim 1, wherein the compound of formula (I) is selected from the group consisting of:

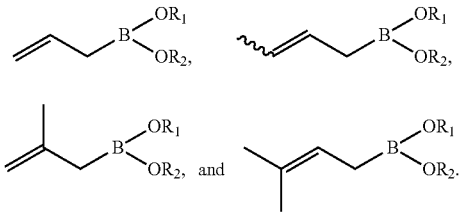

21. The process of claim 1, wherein the compound of formula (I) is selected from the group consisting of:

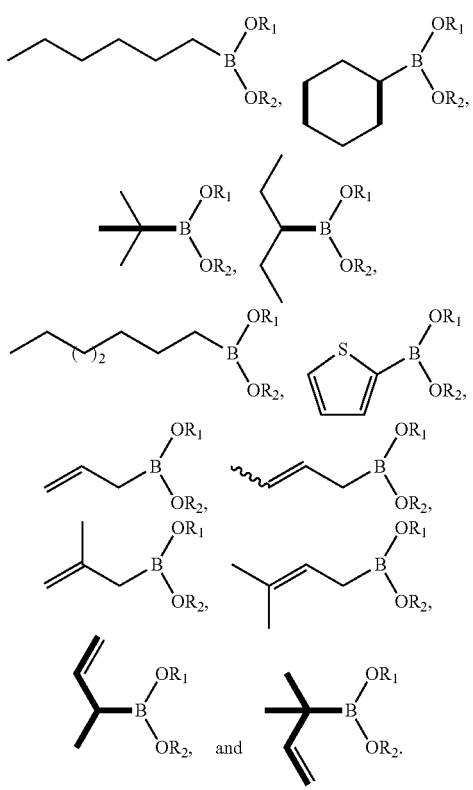

22. The process of claim 3, wherein the halide is chloride, bromide or iodide.

23. The process of claim 1, wherein the reaction temperature is from 20° C. to 30° C.

24. The process of claim 8, wherein $R_4$ is a C5-C12 aryl.

25. The process of claim 8, wherein $R_4$ is a C7-C12 arylalkyl.

26. The process of claim 8, wherein $R_4$ is a C2-C10 allyl.

27. The process of claim 8, wherein $R_4$ is selected from the group consisting of but-2-enyl, 2-methylallyl, and 3-methyl-but-2-enyl.

28. The process of claim 8, wherein $R_4$ is a C2-C10 alkenyl.

29. The process of claim 8, wherein $R_4$ is a C1-C10 alkyl.

30. The process of claim 8, wherein $R_4$ is a C4-C8 cycloalkyl.

31. The process of claim 8, wherein $R_4$ is selected from the group consisting of methyl, ethyl, n-propyl, isopropyl, n-butyl, iso-butyl, sec-butyl, tert-butyl, n-pentyl, n-hexyl, n-heptyl, n-octyl, n-nonyl, n-decyl, cyclopentyl, cyclohexyl, cycloheptyl, and cyclooctyl.

32. The process of claim 8, wherein $R_4$ is selected from the group consisting of furanyl and thiophene.

33. The process of claim 8, wherein the compound of formula (II) is selected from the group consisting of:

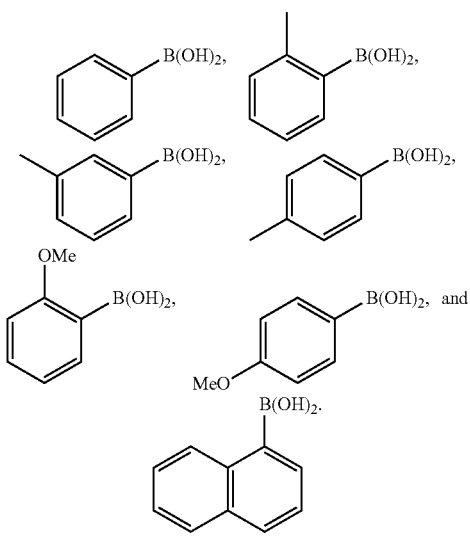

34. The process of claim 8, wherein the Grignard reagent is generated from an $R_4$-halide compound and $Mg^0$.

35. The process of claim 33, wherein the halide is chloride, bromide or iodide.

36. The process of claim 8, wherein the reaction temperature is from −50° C. to +10° C.

* * * * *